(12) United States Patent
Rice et al.

(10) Patent No.: US 8,044,996 B2
(45) Date of Patent: Oct. 25, 2011

(54) SURFACE CONSTRUCTION USING COMBINED PHOTOGRAPHIC AND STRUCTURED LIGHT INFORMATION

(75) Inventors: Bradley W. Rice, Danville, CA (US); Heng Xu, Alameda, CA (US); Chaincy Kuo, Oakland, CA (US)

(73) Assignee: Xenogen Corporation, Alameda, CA (US)

( * ) Notice: Subject to any disclaimer, the term of this patent is extended or adjusted under 35 U.S.C. 154(b) by 949 days.

(21) Appl. No.: 11/429,420

(22) Filed: May 4, 2006

(65) Prior Publication Data

US 2006/0268153 A1 Nov. 30, 2006

Related U.S. Application Data

(63) Continuation-in-part of application No. 11/127,842, filed on May 11, 2005, now Pat. No. 7,298,415.

(51) Int. Cl.
*H04N 13/02* (2006.01)
*G06K 9/00* (2006.01)
*G01B 11/24* (2006.01)

(52) U.S. Cl. .............................. 348/50; 382/154; 356/601
(58) Field of Classification Search .................... 348/46, 348/50, 136, 137, 142; 356/3.1, 12, 601–603, 356/613; 382/154
See application file for complete search history.

(56) References Cited

U.S. PATENT DOCUMENTS

| | | | |
|---|---|---|---|
| 4,687,325 A | 8/1987 | Corby, Jr. | |
| 4,687,352 A | 8/1987 | Igi et al. | |
| 4,773,097 A | 9/1988 | Suzaki et al. | |
| 5,202,091 A | 4/1993 | Lisenbee | |
| 5,205,291 A | 4/1993 | Potter | |
| 5,242,441 A | 9/1993 | Avitall | |
| 5,319,209 A | 6/1994 | Miyakawa et al. | |
| 5,334,193 A | 8/1994 | Nardella | |
| 5,414,258 A | 5/1995 | Liang | |
| 5,452,723 A | 9/1995 | Wu et al. | |
| 5,483,601 A * | 1/1996 | Faulkner | 382/115 |
| 5,530,652 A | 6/1996 | Croyle et al. | |
| 5,584,872 A | 12/1996 | LaFontaine et al. | |
| 5,594,253 A | 1/1997 | Bueno et al. | |
| 5,636,299 A | 6/1997 | Bueno et al. | |
| 5,637,874 A | 6/1997 | Honzawa et al. | |
| 5,650,135 A | 7/1997 | Contag et al. | |

(Continued)

FOREIGN PATENT DOCUMENTS

EP 1 016 419 7/2000

(Continued)

OTHER PUBLICATIONS

Tosovic, et al., "On Combining Shape from Silhouette and Shape from Structured Light", 2002, Proceedings of the 7th Computer Vision Winter Workshop, pp. 108-118.*

(Continued)

*Primary Examiner* — Timothy J Henn
(74) *Attorney, Agent, or Firm* — Beyer Law Group LLP

(57) ABSTRACT

The invention relates to topographic construction that combines photographic and structured light information. The dual modality construction acquires structured light information for an object and photographic images from multiple views about the object. Topographic construction then processes the structured light information and photographic data in the multiple images to generate a surface representation of the object in each modality. The photographic and structured light surface representations are then combined to output a dual modality surface topography.

29 Claims, 18 Drawing Sheets

U.S. PATENT DOCUMENTS

| | | | |
|---|---|---|---|
| 5,661,562 A | 8/1997 | Aharon | |
| 5,672,881 A | 9/1997 | Striepeke et al. | |
| 5,705,807 A | 1/1998 | Throngnumchai et al. | |
| 5,738,101 A | 4/1998 | Sappey | |
| 5,746,210 A | 5/1998 | Benaron et al. | |
| 5,807,262 A | 9/1998 | Papaioannou et al. | |
| 5,812,310 A | 9/1998 | Stewart et al. | |
| 5,818,587 A | 10/1998 | Devaraj et al. | |
| 5,835,617 A | 11/1998 | Ohta et al. | |
| 5,840,572 A | 11/1998 | Copeland et al. | |
| 5,865,754 A | 2/1999 | Sevick-Muraca et al. | |
| 5,867,250 A | 2/1999 | Baron | |
| 5,953,446 A | 9/1999 | Opsal et al. | |
| 5,963,658 A | 10/1999 | Klibanov et al. | |
| 5,970,164 A | 10/1999 | Bamberger et al. | |
| 6,069,698 A | 5/2000 | Ozawa et al. | |
| 6,108,576 A | 8/2000 | Alfano et al. | |
| 6,175,407 B1 | 1/2001 | Sartor | |
| 6,205,243 B1 | 3/2001 | Migdal | |
| 6,205,347 B1 | 3/2001 | Morgan et al. | |
| 6,208,886 B1 | 3/2001 | Alfano et al. | |
| 6,217,847 B1 | 4/2001 | Benaron et al. | |
| 6,219,566 B1 | 4/2001 | Weersink et al. | |
| 6,242,743 B1 | 6/2001 | DeVito et al. | |
| 6,252,623 B1 | 6/2001 | Lu et al. | |
| 6,264,610 B1 | 7/2001 | Zhu | |
| 6,267,477 B1 | 7/2001 | Karpol et al. | |
| 6,321,111 B1 | 11/2001 | Perelman et al. | |
| 6,332,087 B1 | 12/2001 | Svenson et al. | |
| 6,364,829 B1 | 4/2002 | Fulghum | |
| 6,373,557 B1 | 4/2002 | Mengel et al. | |
| 6,377,353 B1 | 4/2002 | Ellis | |
| 6,381,302 B1 | 4/2002 | Berestov | |
| 6,392,241 B1 | 5/2002 | Rushbrooke et al. | |
| 6,394,965 B1 | 5/2002 | Klein | |
| 6,415,051 B1 | 7/2002 | Callari et al. | |
| 6,429,943 B1 | 8/2002 | Opsal et al. | |
| 6,529,627 B1 | 3/2003 | Callari et al. | |
| 6,549,288 B1 | 4/2003 | Migdal et al. | |
| 6,563,499 B1* | 5/2003 | Waupotitsch et al. | 345/420 |
| 6,597,931 B1 | 7/2003 | Cheng et al. | |
| 6,615,061 B1 | 9/2003 | Khalil et al. | |
| 6,615,063 B1 | 9/2003 | Ntziachristos et al. | |
| 6,618,152 B2 | 9/2003 | Toida | |
| 6,618,463 B1 | 9/2003 | Schotland et al. | |
| 6,628,401 B2 | 9/2003 | Toida | |
| 6,628,747 B1 | 9/2003 | Schotland et al. | |
| 6,636,755 B2 | 10/2003 | Toida | |
| 6,642,953 B1 | 11/2003 | Nieto Velasco et al. | |
| 6,646,678 B1 | 11/2003 | Kobayashi | |
| 6,690,520 B1 | 2/2004 | Kusuzawa | |
| 6,710,770 B2 | 3/2004 | Tomasi et al. | |
| 6,775,349 B2 | 8/2004 | Schotland et al. | |
| 6,775,567 B2 | 8/2004 | Cable et al. | |
| 6,813,030 B2 | 11/2004 | Tanno | |
| 6,919,919 B2 | 7/2005 | Nelson et al. | |
| 6,963,375 B1 | 11/2005 | Lundberg | |
| 6,965,690 B2* | 11/2005 | Matsumoto | 382/154 |
| 7,184,047 B1 | 2/2007 | Crampton | |
| 7,298,415 B2 | 11/2007 | Nilson et al. | |
| 7,589,786 B2 | 9/2009 | Nilson et al. | |
| 7,595,838 B2 | 9/2009 | Nilson et al. | |
| 2003/0011701 A1* | 1/2003 | Nilson et al. | 348/370 |
| 2003/0099329 A1 | 5/2003 | Schotland et al. | |
| 2004/0010192 A1 | 1/2004 | Benaron et al. | |
| 2004/0015062 A1 | 1/2004 | Ntziachristos et al. | |
| 2004/0021771 A1 | 2/2004 | Stearns | |
| 2004/0085536 A1 | 5/2004 | Schotland et al. | |
| 2004/0089817 A1 | 5/2004 | Long et al. | |
| 2004/0262520 A1 | 12/2004 | Schotland et al. | |
| 2005/0149877 A1 | 7/2005 | Rice et al. | |
| 2005/0283071 A1 | 12/2005 | Ripoll et al. | |
| 2006/0173354 A1 | 8/2006 | Ntziachristos et al. | |

FOREIGN PATENT DOCUMENTS

| | | | |
|---|---|---|---|
| WO | WO97/40381 | 10/1997 | |
| WO | WO98/34533 | 8/1998 | |
| WO | WO 00/17643 | 3/2000 | |
| WO | WO00/36106 | 6/2000 | |
| WO | WO00/54581 | 9/2000 | |
| WO | WO01/18225 | 3/2001 | |
| WO | WO 01/63247 | 8/2001 | |
| WO | WO02/41760 | 5/2002 | |
| WO | 2004/008123 | 1/2004 | |
| WO | WO 2006066791 A1 * | 6/2006 | |

OTHER PUBLICATIONS

Tosovic, S. "Construction of 3D Models of Objects Using Combination of Shape from Silhouette and Shape from Structured Light", Jul. 2001, Vienna University of Technology Pattern Recognition and Image Processing Group Technical Report PRIP-TR-099.*

International Search Report dated Nov. 20, 2007 in PCT Application No. PCT/US06/18203.

Written Opinion dated Nov. 20, 2007 in PCT Application No. PCT/US06/18203.

Arridge, "Photon-Measurement Density Functions. Part 1: Analytical Forms", Applied Optics, vol. 34, No. 31, Nov. 1, 1995, pp. 7395-7409.

Arridge, "Photon-Measurement Density Functions. Part II: Finite-Element-Method Calculations", Applied Optics, vol. 34, No. 34, Dec. 1, 1995, pp. 8026-8037.

Chang et al., "Improved Reconstruction Algorithm for Luminescence Optical Tomography When Background Lumiphore is Present", Applied Optics, vol. 37, No. 16, Jun. 1, 1998, pp. 3547-3552.

Contag et al., "Photonic Detection of Bacterial Pathogens in Living Hosts", Molecular Microbiology, vol. 18, No. 4, 1995, pp. 593-603.

Eppstein et al., "Biomedical Optical Tomography Using Dynamic Parameterization and Bayesian Conditioning on Photon Migration Measurements", Applied Optics, vol. 38, No. 10, Apr. 1, 1999, pp. 2138-2150.

Ghiglia et al., "Two-Dimensional Phase Unwrapping: Theory, Algorithms, and Software", Wiley-Interscience publication, 1998, ISBN 0-471-24935-1, p. 312.

Haskell et al., "Boundary Condition for the Diffusion Equation in Radiative Transfer", Optical Society of America, vol. 11, No. 10, Oct. 1994, pp. 2727-2741.

Ntziachristos et al., "Experimental Three-Dimensional Fluorescence Reconstruction of Diffuse Media by Use of a Normalized Born Approximation", Optical Society of America, vol. 26, No. 12, Jun. 15, 2001, pp. 893-895.

Ntziachristos et al., "Fluorescence molecular tomography resolves protease activity in vivo," Nature Medicine, vol. 8, No. 7, Jul. 2002, pp. 757-760.

Rice et al., "In Vivo Imaging of Light-Emitting Probes", Journal of Biomedical Optics, vol. 6, No. 4, Oct. 2001, p. 432-440.

Tuchin, "Tissue Optics: Light Scattering Methods and Instruments for Medical Diagnosis", SPIE Press, 2000.

Weissleder et al., "In Vivo Imaging of Tumors with Protease-Activated Near-Infrared Fluorescent Probes", Nature Biotechnology, vol. 17, Apr. 1999, pp. 375-378.

Windsor et al., "Imaging Pulmonary Inflammation Using Fluorescence Molecular Tomography," Society for Molecular Imaging, Sep. 23, 2005.

Yang et al., "Whole-Body Optical Imaging of Green Fluorescent Protein-Expressing Tumors and Metastases", PNAS, vol. 97, No. 3, Feb. 1, 2000, pp. 1206-1211.

Zhang et al., "Rapid In Vivo Functional Analysis of Transgenes in Mice Using Whole Body Imaging of Luciferase Expression", Transgenic Research, vol. 10, 2001, pp. 423-434.

Benaron, David A., "A System for Imaging Infection and Gene Expression in the Body in 3-D," Biomedical Optical Spectroscopy and Diagnostics, 1998 Technical Digest, 1998, Optical Society of America, pp. 134-135.

Frohn, "Super-Resolution Fluorescence Microscopy by Structured Light Illumination," Dissertation submitted to the Swiss Federal Institute of Technology, Zurich, 2000.

Mahmood et al., "Near-Infrared Optical Imaging of Protease Activity for Tumor Detection," Radiology, Dec. 1999, pp. 866-870.

Rice et al., "Advances in 2D In Vivo Optical Imaging Instrumentation," Abstract No. 186, Society for Molecular Imaging 2$^{nd}$ Annual Meeting, Aug. 2003.

Takeda et al., Fourier Transform Method of Fringe-Pattern Analysis for Computer-Based Topography and Interferometry, J. Opt. Soc. Am., vol. 72, No. 1, Jan. 1982.

Toyooka et al., "Automatic Profilometry of 3-D Diffuse Objects by Spatial Phase Detection," Applied Optics, vol. 25, No. 10, May 15, 1986.

Weissleder et al., "Shedding Light Onto Live Molecular Targets," Nature Medicine, vol. 9, No. 1, Jan. 2003, pp. 123-128.

Research & Development (magazine), vol. 42, No. 9, Sep. 2000, Part 1 of 2.

International Search Report dated Feb. 8, 2008 in PCT Application No. PCT/US07/10485.

Written Opinion dated Feb. 8, 2008 in PCT Application No. PCT/US07/10485.

Office Action dated Jun. 26, 2008 in U.S. Appl. No. 11/127,346.

Office Action dated Mar. 21, 2007 in U.S. Appl. No. 11/127,842.

Office Action dated Sep. 2, 2010 for U.S. Appl. No. 11/871,062.

Supplementary Search Report dated Jul. 25, 2011 from European Application No. 06759546.2.

Office Action dated Jul. 22, 2011 from U.S. Appl. No. 11/871,062.

\* cited by examiner ic representation. For example, in vivo optical imaging
SURFACE CONSTRUCTION USING COMBINED PHOTOGRAPHIC AND STRUCTURED LIGHT INFORMATION

CROSS-REFERENCE TO RELATED APPLICATIONS

The application is a continuation-in-part of prior application No. 11/127,842, filed May 11, 2005, now U.S. Pat. No. 7,298,415, from which priority under 35 U.S.C. §120 is claimed.

FIELD OF THE INVENTION

The present invention relates generally to systems and methods for constructing a surface representation of an object. In particular, the invention relates to systems and methods that create topographic representations of an object using photographic and structured light information.

BACKGROUND OF THE INVENTION

Topographic reconstruction refers to the practice of creating a surface representation of an object.

Numerous applications rely on obtaining an object's topographic representation. For example, in vivo optical imaging involves the capture of light emitted from within an object. A source of the light inside the object indicates a portion of the object where an activity of interest may be taking place. In one imaging application, the object is a small animal such as a mouse and the low intensity light source includes tumor cells that are being tracked and are labeled with a light-emitting reporter, such as firefly luciferase or a fluorescent protein or dye. Diffuse tomography techniques can be used to determine the location and brightness of labeled cells. However, these techniques require accurate measure of the surface topography of the animal subject.

There are difficulties associated with obtaining surface representations for small objects such as mice. Each mouse has a unique size, and its shape changes each time the mouse is anesthetized and imaged. These realities demand that topographic reconstruction occur efficiently and without excessive time (or labor) for each mouse or new object. In addition, mice include surface features that complicate topographic measurement: concave surface features can be tough to detect with an external and distant camera; and fur or folds in the skin increasingly introduce noise for surface measurements as surface resolution increases. Structured light topography, which casts a series of closely spaced lines onto the object and detects deformation in the lines resulting from the shape of the object, often errs when the inter-line spacing nears the resolution of surface features on the object such as mouse fur and high curvature regions.

Currently, there is no topographic reconstruction technology that both a) services complex surfaces and high detail needed for imaging applications such as in vivo optical imaging and b) permits easy and efficient production of a high definition surface representation. In view of the foregoing, new techniques for obtaining topography of a small object are desirable.

SUMMARY OF THE INVENTION

The present invention improves topographic construction by combining photographic and structured light information. The dual modality construction acquires structured light information for an object and photographic images from multiple views about the object. Topographic construction then processes the structured light information and photographic data in the multiple images to generate a surface representation of the object in each modality. The photographic and structured light surface representations are then combined to output a dual modality topography.

For photographic surface construction, the methods capture and store multiple photographic images. A back-projection method is then used to process data in the photographic images to generate a surface topography. In one embodiment, this includes constructing a 2D mask for each view of multiple views, and then combining the 2D mask of each view to form a 3D surface representation. This method is fast and robust, but may fail to resolve concave features on an object surface.

Structured light transmits a set of lines onto an object from an angle. The lines are displaced, or phase shifted relative to a stage, when they encounter an object with finite height, such as a mouse. A camera captures a structured light image and the surface topography for the object (over its entire surface or a portion facing the camera) is determined by analyzing the phase shift of the lines. A quality measure may also be applied to the structured light information to permit quality assurance on the 3D structured light representation. The structured light method is good at resolving concave features in the surface, but is more susceptible to surface flaws such as rough fur or wrinkles in the skin.

Combined, the two methods overcome limitations of each method individually, and produce improved topographic representations.

In one aspect, the present invention relates to a method of constructing a topographic representation of at least a portion of an object. The method includes obtaining at least one photographic image of the object that includes photographic information. The method also comprises obtaining a structured light image of the object that includes structured light information. The method further comprises constructing the topographic representation of at least the portion of the object using a combination of topographic information from the structured light image and topographic information from the photographic image.

In another aspect, the present invention relates to a method of constructing a topographic representation. The method includes obtaining multiple photographic images of the object that correspond to multiple views of the object relative to at least one camera. The method also includes constructing a photographic topographic representation of at least a portion of the object using photographic information form the multiple photographic images. The method further includes obtaining a structured light image that includes topographic information of the object. The method additionally includes constructing the topographic representation of at least the portion of the object using a combination of the structured light topographic information and topographic information from the photographic topographic representation.

In yet another aspect, the present invention relates to an imaging system. The system includes at least one camera configured to capture a photographic image of the object. The system also includes a structured light source adapted to cast structured light onto the object and generate structured light information. The system further includes a processor that uses instructions stored in memory to construct the topographic representation of at least the portion of the object using a combination of topographic information from a structured light image captured by the at least one camera and topographic information from a photographic image captured by the at least one camera.

In still another aspect, the present invention relates to a computer readable medium including instructions for creating a topographic representation for at least a portion of an object.

These and other features of the present invention will be described in the following description of the invention and associated figures.

DETAILED DESCRIPTION OF THE PREFERRED EMBODIMENTS

Figure 1:
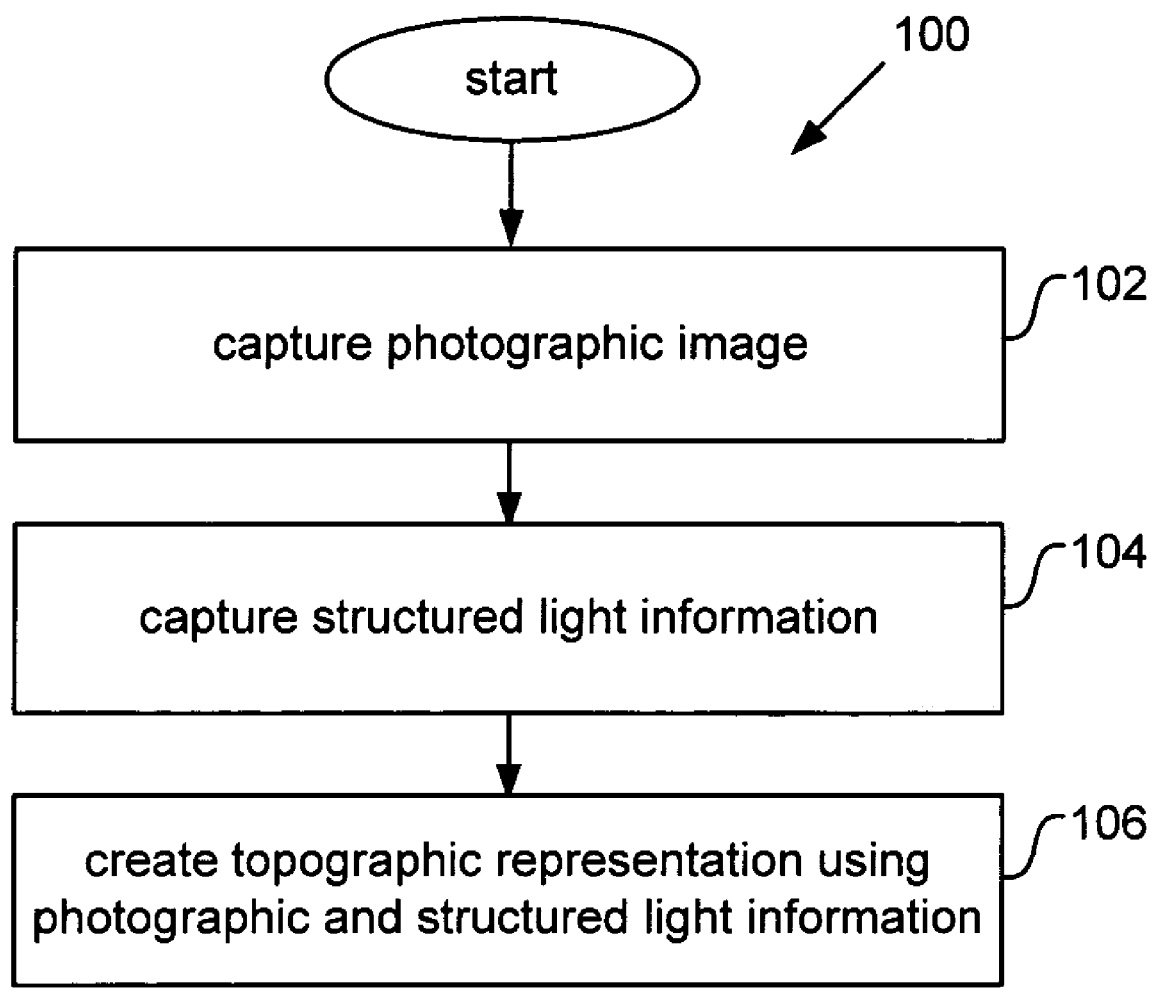
FIG. 1 shows topographic reconstruction in accordance with one embodiment of the present invention.

The present invention is described in detail with reference to a few preferred embodiments as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

The present invention employs a combination of structured light and photographic information to build a topographic representation of an object. The topographic construction employs information from both modalities: structured light provides high detail surface information, while the back-projection photography provides a robust and fast secondary source of topographic information. Either modality may be used as a secondary source that verifies or improves the other and overcomes limitations and deficiencies of the other. For example, the photographic information may be used to remedy structured light inaccuracies of structured light imaging at high resolution that result from the presence of hair, wrinkles, scars, rough surfaces, and high curvature regions such as arms and legs of a mouse. The photographic information, however, often fails to detect concave features on the object, which the structured light data remedies. This dual modality topographic construction improves accuracy and reliability of topographic output relative to either modality alone.

The combination also provides a robust solution for obtaining surface representations of small objects such as mice that does not add significant resources to an imaging system. From a hardware perspective, the present invention simply adds photographic capture hardware (e.g., lights and a camera) to an apparatus that employs structured light. These photographic hardware components may already be present, and the two modalities can use the same camera. The invention adds software requirements for combining information from both modalities, which can be done via software updates for systems that already include hardware for both modalities.

As the term is used herein, a "photographic" image refers to a greyscale and/or color image of an object (or a portion thereof) acquired using a camera (or the like for capturing a light image) and when illuminated by a broad or smooth (or non-structured) light source, such as an LED or a tungsten lamp. The photographic image includes light information that gives a contrast between the object (e.g. a mouse) and the background. This contoured contrast may be referred to as a mouse mask, which resembles a 2D mouse outline in the photographic image. A structured light image may broadly be considered as a photograph, but differs in that the illumination source provides structured light, and the structured light image only captures information illuminated by the structured light. Further description of structured light and structured light sources is provided below.

As the terms are used herein, 'surface' and 'topographic' are used interchangeably and refer to the exterior boundary of an object. A 'surface representation' refers to data that describes the exterior boundary of an object (such as x,y,z coordinates in a 3-dimensional space), and may include any suitable data structure or mathematical representation for doing so. For example, a surface representation of a mouse may be saved as a file or array of x,y,z surface coordinates for a mouse. Other mathematical representations and data structures are also suitable for use. The terms 'topographic reconstruction' or 'topographic construction' refer to the process of building a surface representation, and are used interchangeably herein.

FIG. 1 shows a flowchart 100 for simplified topographic construction in accordance with one embodiment of the present invention. While the present invention will now be discussed as methods and discrete steps for topographic construction, those of skill in the art will appreciate that the methods and steps also describe systems and components for creating a topographic representation.

Figure 4:
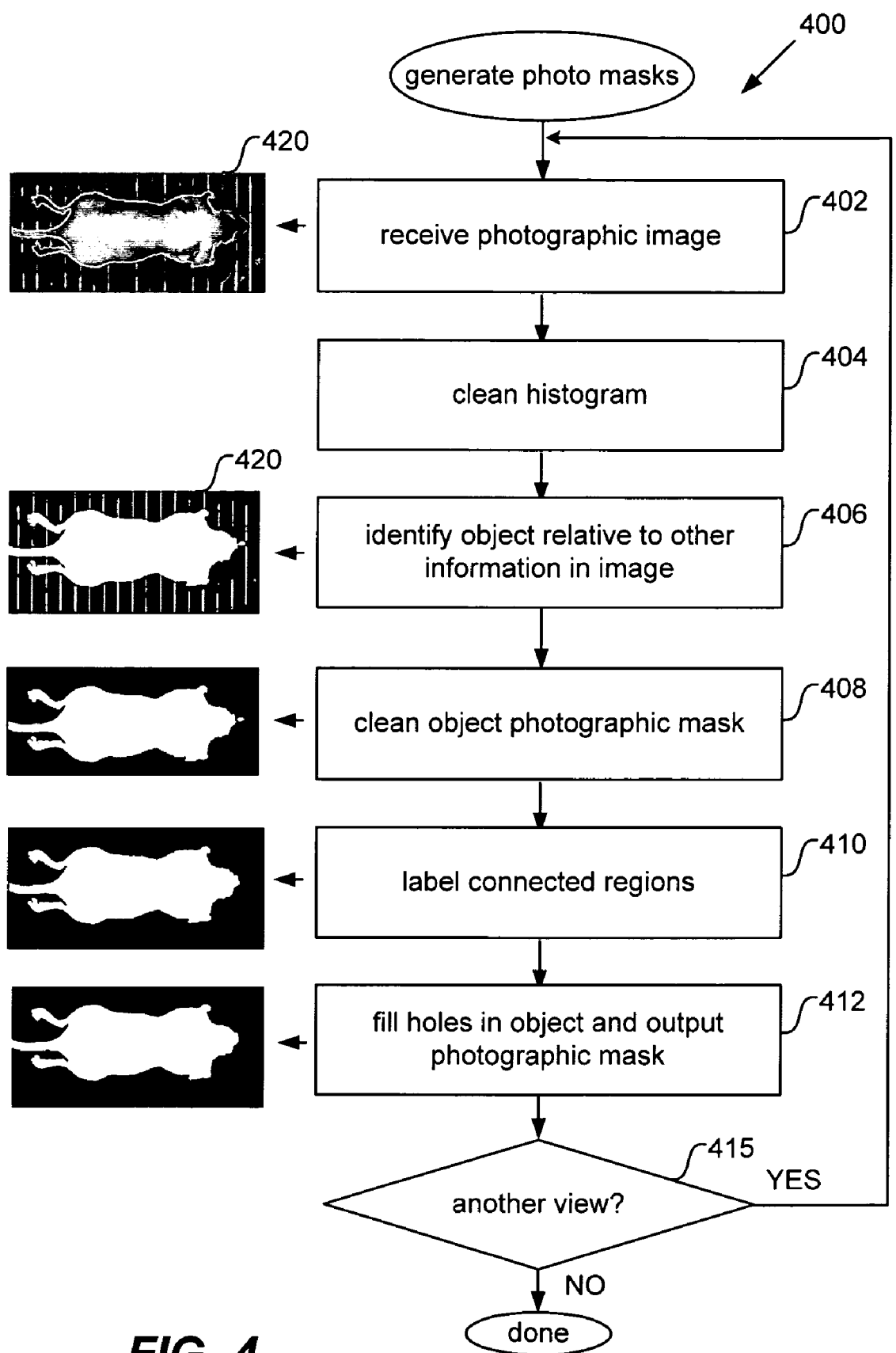
FIG. 4 shows a process flow for obtaining a photographic mask from a photographic image in accordance with a specific embodiment of the present invention.

Flowchart 100 captures at least one photographic image of the object using a camera (102). In one embodiment, multiple photographic images are captured from multiple views. The multiple photographic images permit collective back-projection analysis to build a surface topography of the object, which uses 2D projections of the object from different and multiple angles (shadows or outlines of the object). FIGS. 4-5 describe this back-projection photographic construction in more detail. Output from step 102 includes one or more photographic images, photographic data in these images and/or a photographic topography of the object.

Figure 8A:
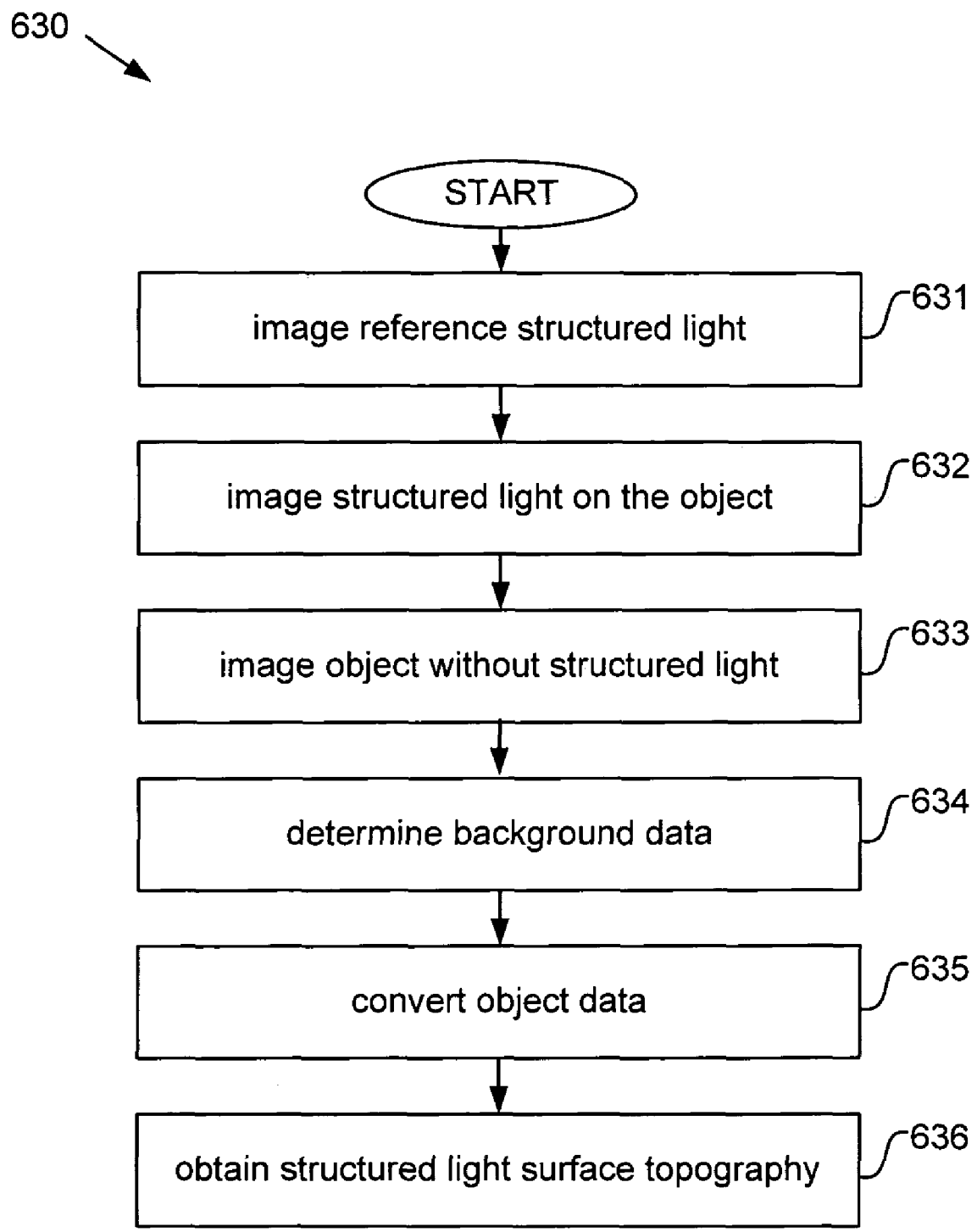
FIG. 8A illustrates a process flow for obtaining surface topography data in accordance with one embodiment of the present invention.
Figure 8B:
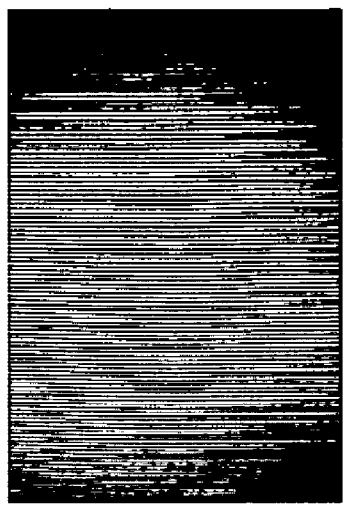
FIGS. 8B-8H illustrate pictorial representations of structured light imaging corresponding to the process flow of FIG. 8A.

Image capture also include obtaining structured light images and information of the object (104). Structured light uses a set of lines of light to determine height information for an object. The lines are cast onto the object from an angle displaced from the optical axis and are phase shifted relative to an underlying surface or stage, when they encounter an object with finite height such as a mouse. This phase shift is analyzed to produce a surface topography for the object. A camera captures the structured light information. FIG. 8A describes one suitable structured light process in more detail.

Figure 2:
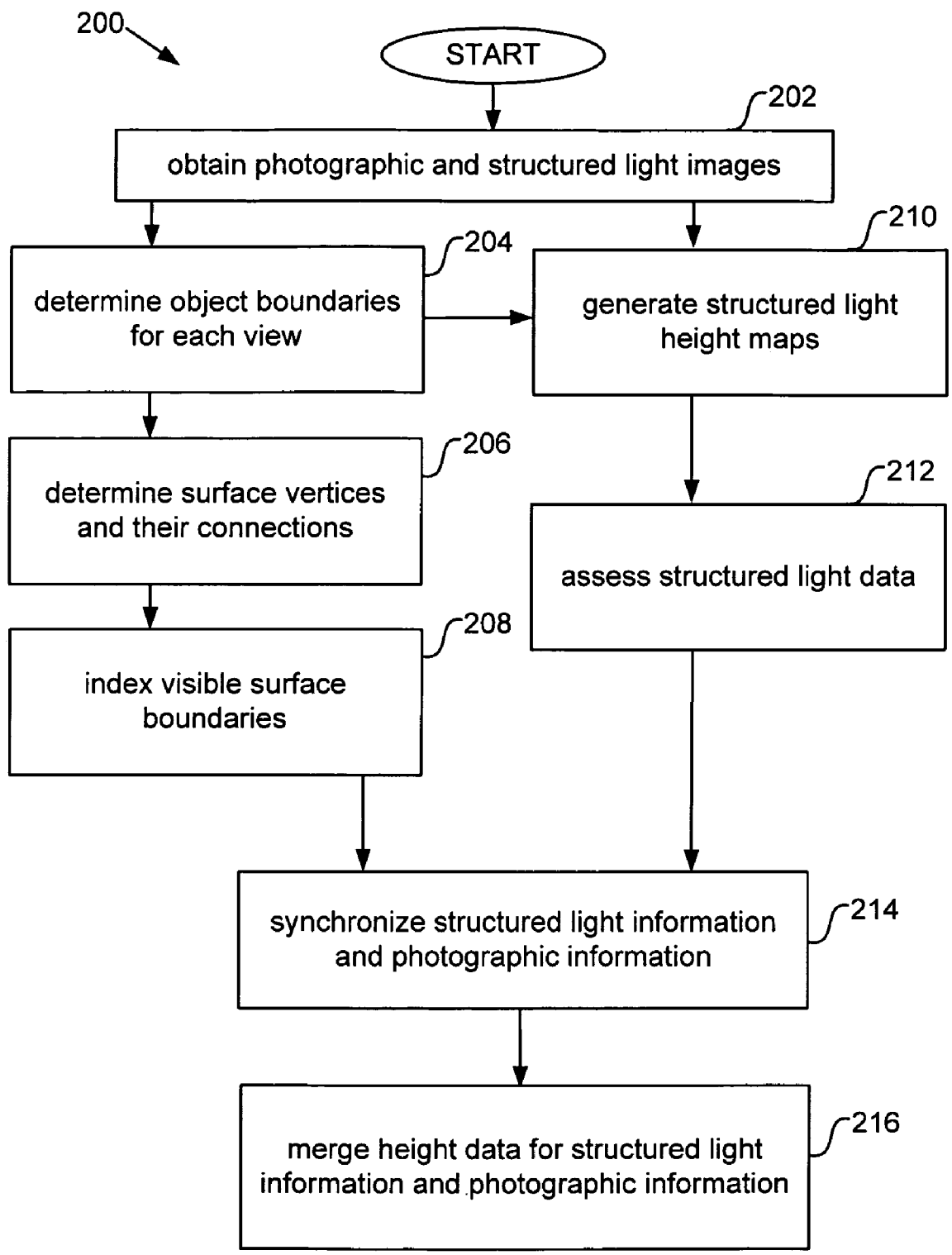
FIG. 2 illustrates a method for dual modality topographic reconstruction in accordance with one embodiment of the present invention.

In one embodiment, the set of lines is projected down on an object at an angle (at about 30 degrees, for example) to a surface normal (see FIG. 2). The object generates structured light surface information as each light line reacts to the shape of the animal. Cumulatively, the lines of light each bend or alter in spacing as they pass over the object. The structured light surface information can be measured and used to determine the height of the surface at all locations that are illuminated by the structured light source. A camera captures the structured light surface information, and may digitize the information to facilitate further processing. Output from step 104 includes one or more structured light images and height data for the object in the form of structured light information.

Figure 3:
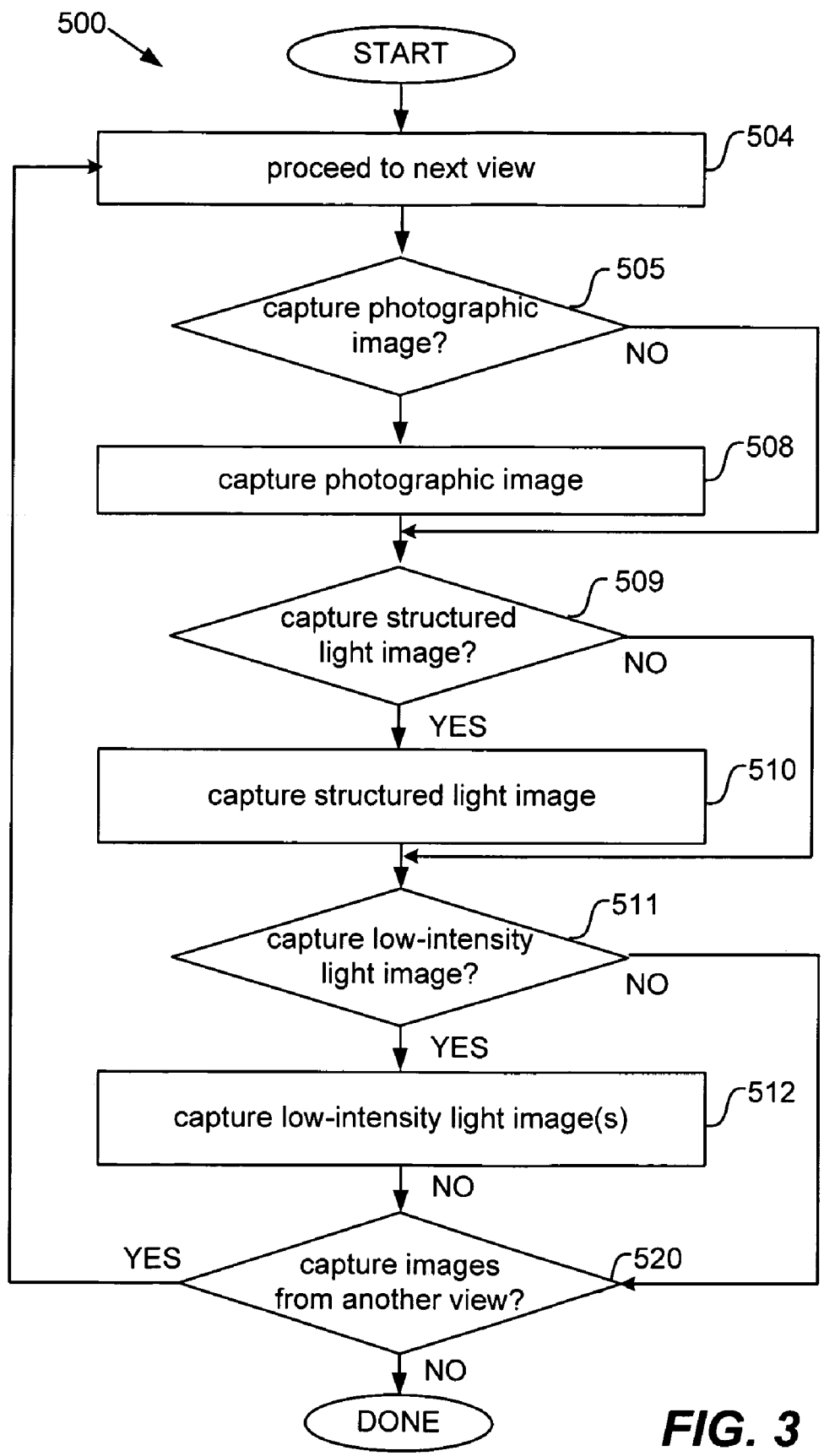
FIG. 3 describes image capture in accordance with one embodiment of the invention.

Image capture is not restricted to any order; photographic image capture and structured light image capture may occur serially, together at each position of the object relative to a camera and a multiple positions, etc. Image capture may also include using one or more stored images of the object (e.g., old photographic images of the object) from memory. FIG. 3 describes image capture in accordance with one embodiment of the invention.

Topographic reconstruction then continues with creating a topographic representation of at least a portion of the object using a combination of the structured light information and photographic information (106). The process may construct a structured light topography (see FIG. 8A), construct a photographic topography, and use information from both. For example, the topographic reconstruction may use one modality to modify and improve the other. Typically, the structured light representation has surfaces and a starting orientation that reasonably resemble the final topographic output produced by reconstruction 100. In other words, only minor adjustments to the structured light data, such as corrections for deficiencies in the structured light representation, may be needed and made. If discrepancies are present in the structured light data, then the photographic information is used to overcome the discrepancies. In another embodiment, the photographic information is used to construct a rough frame of the object. The more accurate height information from the structured light reconstruction is then used in locations where the structured light quality is good (according to a quality determination of the structured light information, as will be described further below).

Using software that employs a structured light and photographic analysis as described below, a processor generates surface topography data for at least a portion of the object. The portion may include the surfaces of the object that face the camera, or smaller segments thereof. In another embodiment, the present invention builds a larger surface topography that is greater than just the surface facing the camera. In this case, an imaging system captures images from multiple views (see FIG. 3). Surface representations from multiple views of the object (e.g., top, bottom, sides, or other angles) allow generation of a three-dimensional surface representation for the entire object.

Various reconstruction techniques may be stored in software and used to build a 3D topographic representation. In one embodiment, the surface topography reconstruction produces a surface mesh. The subsequent methods described herein characterize actions implemented in software to construct a topographic representation of an object.

FIG. 2 illustrates a method 200 for dual modality topographic reconstruction in accordance with one embodiment of the present invention.

Method 200 begins with obtaining photographic and structured light images (202). This includes: a) image capture from a single position, which builds topography of surfaces that face the camera at that position, or b) image capture from multiple angles and views (FIG. 3) to enable a larger surface reconstruction. Additional image processing steps may be taken to clean information in the images, such as filtering or cropping photographic images to obtain a reduced region of a photo that contains relevant information. As shown, processing on the photographic and structured light images occurs in parallel; that is, each may occur individually at any time.

Photographic processing first determines 2D object boundaries for the object in each photographic image (204 and FIG. 4). This 'photomasking' applies one or more image-processing techniques to separate portions of an image that are part of the object from portions of the image that are not. Image processing techniques used in this regard may include any image data manipulation algorithms suitable for identifying an object or its boundary in a photographic image, such as histogram manipulation techniques that clean the image (e.g., compressions and shifts to reduce noise), threshold techniques to differentiate the object from the background, or erosion/dilution techniques to clean boundary lines, and filling techniques to further identify the object and clean output. Output of this step includes a boundary or perimeter of the object in each photographic image, commonly stored as a data file. Photomasking is then and is repeated for each image and/or view.

Figure 5A:
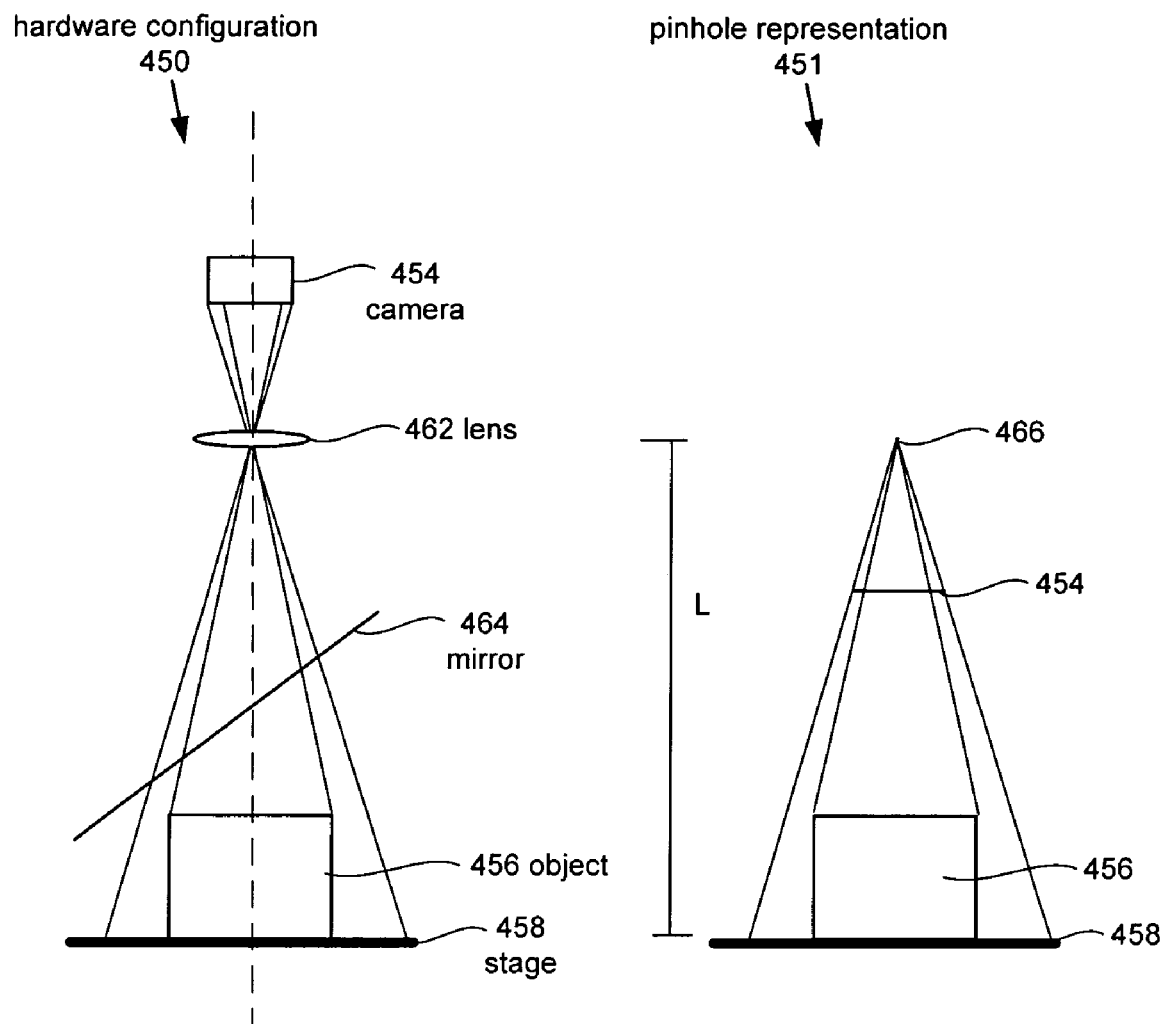
FIG. 5A shows the conversion of hardware parameters used in photographic image capture into a representative 3D space (in software) according to a 'pinhole' model.
Figure 5C:
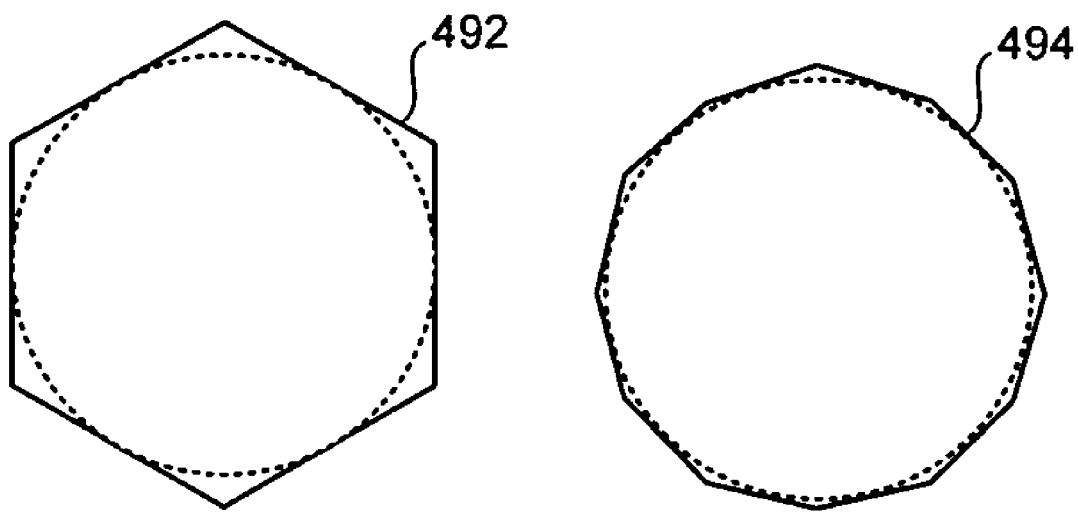
FIG. 5C illustrates the effect of increasing the number of views for 3D photographic topography.
Figure 6:
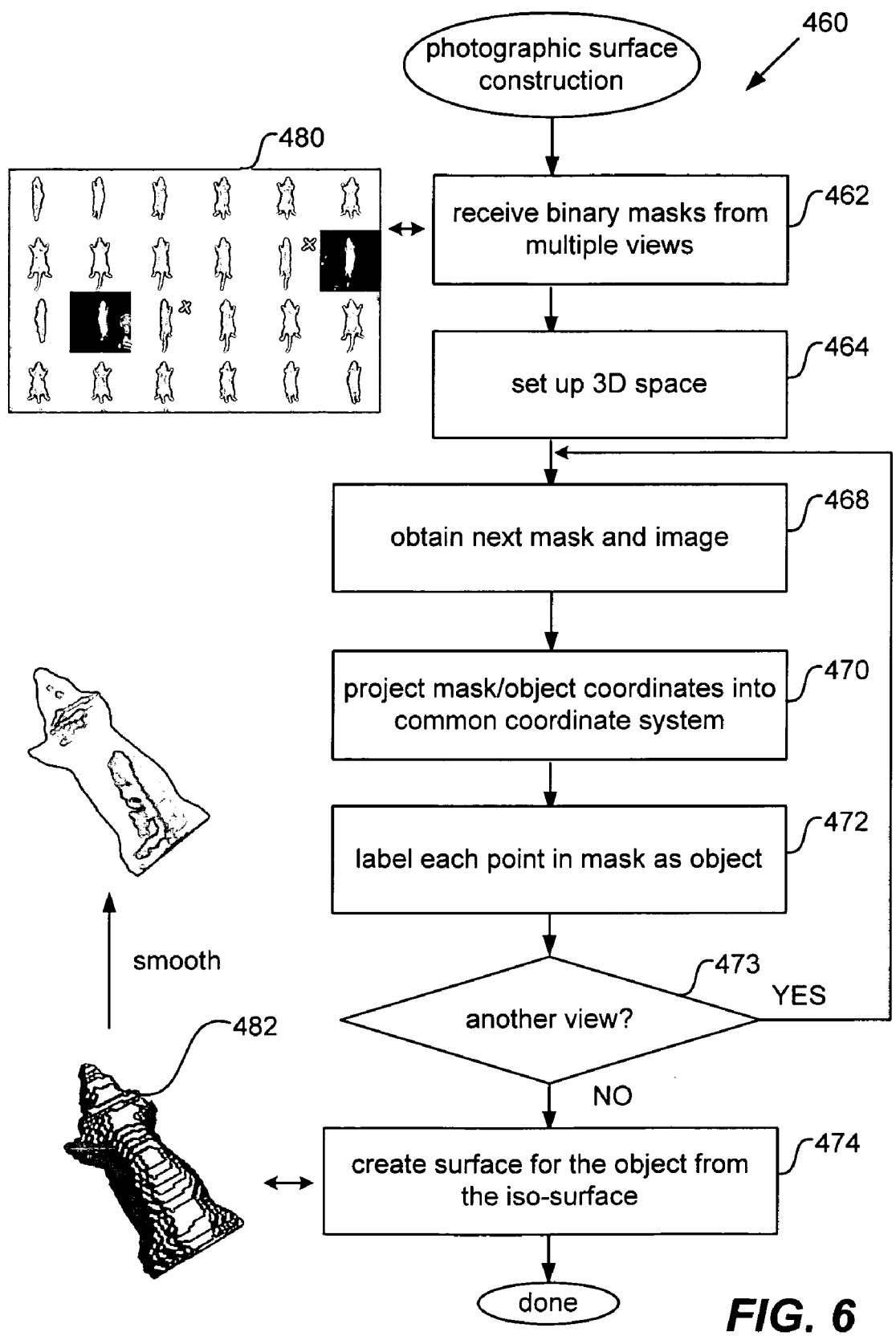
FIG. 6 illustrates a method for photographic 3D surface construction in accordance with a specific embodiment of the present invention.

Photographic topographic processing then performs surface reconstruction using the cleaned images from multiple views (206 and FIG. 6). One photographic reconstruction technique loops through each image/view and collects perimeter position points identified as the object in each view. The perimeter/surface points from each view, along with the known position of each image in 3D space relative to the camera, permits each object point to be mapped into a 3D space. Cumulatively, all points identified as the object in the 3D space then form a 3-D representation. The accuracy of this technique will depend on the number of views and images used, as described in further detail below with respect to FIG. 5C. Photographic surface reconstruction may also smooth surfaces created in this manner.

Figure 5B:
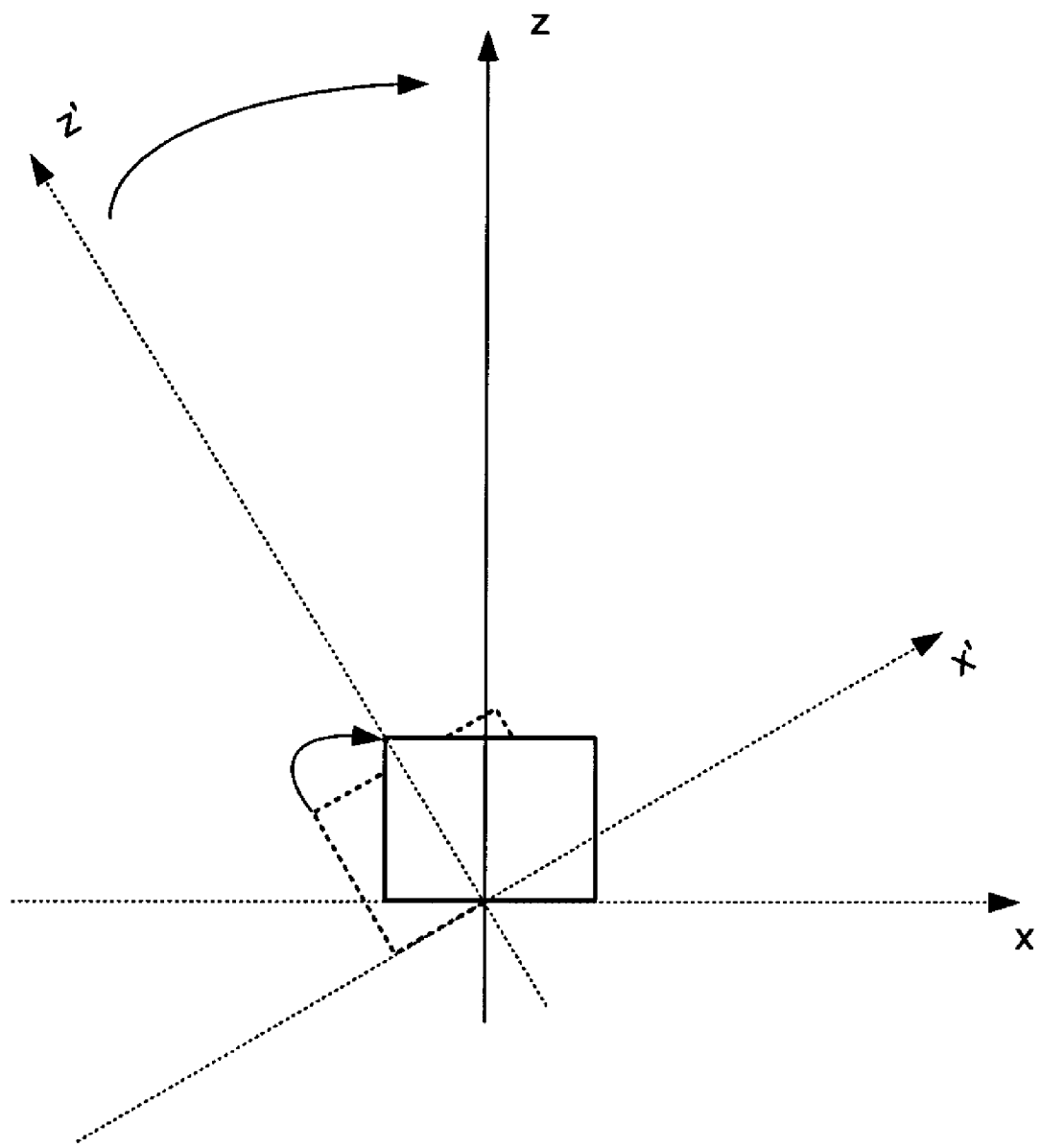
FIG. 5B shows the conversion of photographic information from different views to a common perspective.

Photographic topographic processing then maps visible surface boundaries of the object into a coordinate system suitable for comparison with the structured light information (208 and FIG. 5B). In a specific embodiment, this conversion takes object and surface definitions determined in step 206 and performs a 3-D space translation and/or rotation to provide surface coordinates for the object that match a view from the camera used in the structured light imaging.

Structured light processing receives the structured light images from 202 and performs structured light topographic reconstruction to obtain height maps and optionally quality maps from the images (210 and FIG. 8A). Typically, this includes determining a phase shift from the structured light lines in an image and then unwrapping the phase to get a surface mesh, or height map. A reference, or background, surface may also be subtracted from the object surface, to yield a final surface representation. As one of skill in the art will appreciate, there are numerous algorithms suitable for use with the present invention to reconstruct a surface from structured light images. For example, the phase shift of each line at all points on the image can be determined from a 2D Fourier transform. The actual surface height is then computed by "unwrapping" the Fourier phase map.

Figure 9:
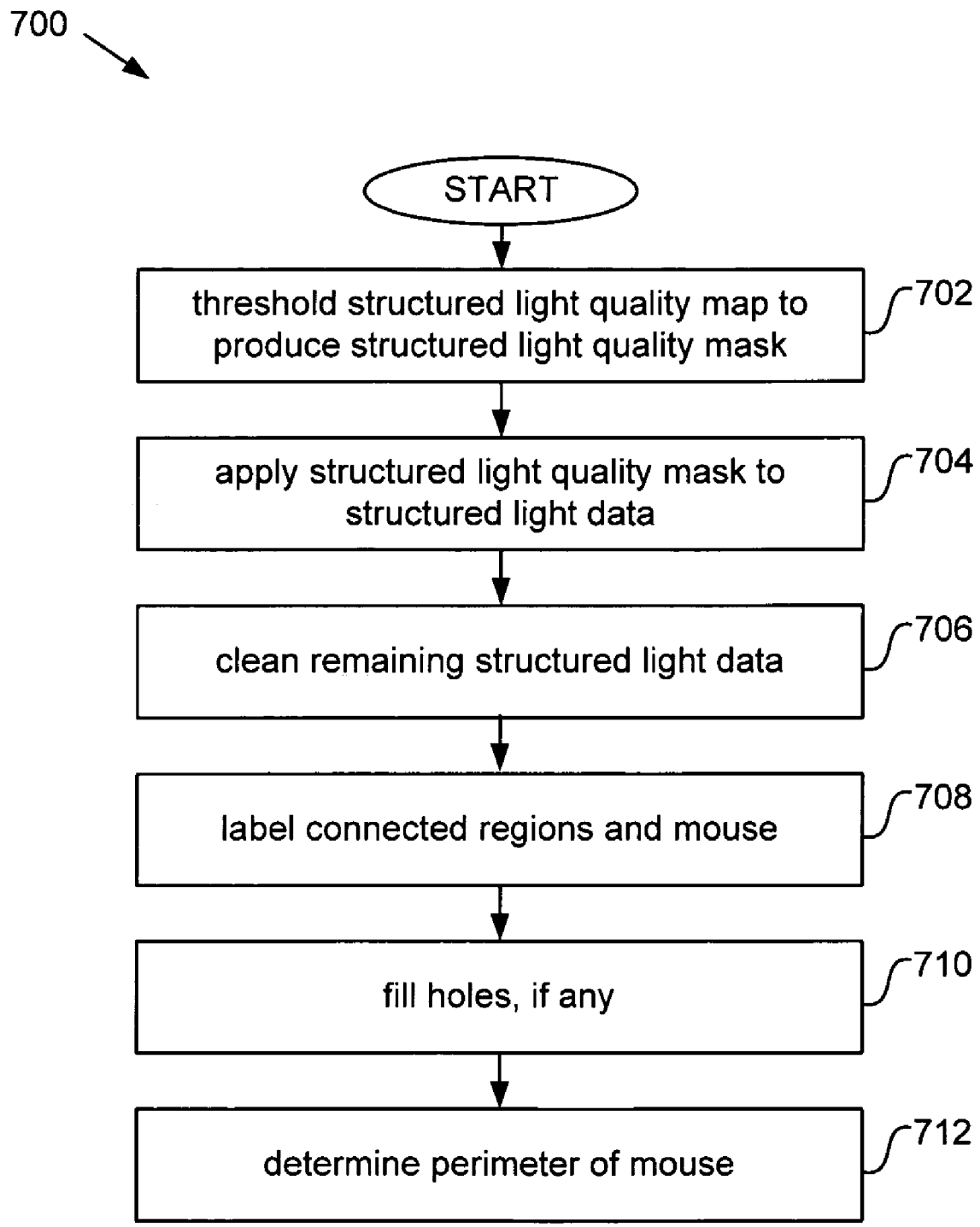
FIG. 9 illustrates a method for modifying a structured light image using quality in accordance with a specific embodiment of the present invention.

The structured light output may then be subject to one or more image processing techniques to improve output (212 and FIG. 9). For example, applying a quality threshold to the structured light information creates a binary mask that filters and separates quality portions of the structured light images from other portions not suitable for further processing. The filtered output may be further processed using erosion/dilution techniques to clean edges of the object in the image. Output of this step includes quality thresholded structured light images.

The dual modality topographic reconstruction then synchronizes the structured light information and the photographic information and labels the height information (214). This overcomes any offset in the dual modality information between shape or position of the object as obtained in structured light imaging relative to the shape or position of the object determined in photographic imaging. Output of this step includes labels for all surface vertices under a common coordinate system. For example, each view may be labeled with x,y,z coordinates where the x and y coordinates refer to planar coordinates of an image while the z coordinate refers to height of the object out of the image plane. The x,y,z coordinates then permit comparison of the structured light information and the photographic information.

Topographic reconstruction 200 then merges the height information from both modalities and chooses height information from whichever modality (at each point on the surface) provides better data (216). In a specific embodiment, height given by the structured light information replaces height information from the photographic images for most surfaces of the object, save where quality is low in the structured light images. For example, regions of the structured light images, such as where quality suffered due to excessive line bending or noise features on the mouse diminished structured light quality, are flagged in step 212 and then not used in step 216. At these surface portions, photographic information is then used to approximate object topography. Some smoothing operations may be used to account for slope omissions or discrepancies along planar directions of the reconstruction that are normal to the height. Output of this step is a 3D topography for the object that includes both structured light height information and height information from photographic image processing.

In general, the present invention is not limited to any particular object being imaged. In one embodiment, the object is small and less than two liters in volume. In another embodiment, the object is anything that fits within an imaging chamber or imaging box such as that described below with respect to FIGS. 10-12. Alternatively, the object is sized such that structured light lines cast upon the object cover it (or a portion of the object) at a desired spacing suitable for structured light imaging. The remaining disclosure will describe a mouse or small animal as an object to be imaged. Mice present complex and unique surfaces that vary for each mouse and necessitate individual and expeditious topographic reconstruction. The mouse is usually anaesthetized during image capture to minimize movement.

Individual steps in topographic reconstruction 200 will now be expanded upon.

The present invention is not limited to how or when images are captured. Moving forward, image capture will be described with respect to: a) using a single imaging system and b) capturing images relatively at the same time (e.g., within half an hour). Leg position for a mouse may vary each time the mouse is anaesthetized, so carrying out all imaging during one slumber and on a common stage without moving the mouse permits imaging to occur with less variation in mouse shape. Suitable imaging systems for capturing multiple photographic and structured is described below with respect to FIGS. 10-12. Other imaging systems may be used for photographic and/or structured light image capture. Images may come from separate imaging systems or sources, and at unrelated times when stored in memory.

Turning now to FIG. 3, process flow 500 illustrates a method of capturing multiple photographic, structured light and, if desired, luminescent images in accordance with one embodiment of the present invention.

The photographic and structured light images are taken from different views of the mouse. The different views refer to different angles or positions of the mouse relative to a camera during image capture. Process flow 500 begins by obtaining a next view (504). There are numerous ways to produce multiple views of an object. In one embodiment, the mouse rests on a stage that moves relative to a fixed camera. Stages that move in 1-D and 2-D are described in further detail below (see FIGS. 10-12). In another embodiment, the mouse is stationary and the camera moves. Multiple cameras may also be employed to produce multiple views for a stationary mouse. Lastly, both the object and camera may move. Any of these configurations is suitable to provide multiple views of the object.

Suitable multi-view imaging systems are described below with respect to FIGS. 10-12. In this case, the mouse rests on a moveable stage in an imaging chamber and process flow 500 begins by placing the animal on the stage within the imaging box. The stage may also include anesthesia delivery to keep the mouse sedated and still. Using a computer that controls the system or acts as an interface, a user inputs a desired view or position for the mouse. Based on the input, a transport mechanism moves the stage to the corresponding position according to a control signal provided by the computer. In FIGS. 12A-12C, stage 74 may include a transparent bottom, so that the subject can be imaged from the bottom side. For example, stage 74 may be constructed of an aluminum frame with a grid of thin nylon threads to support the subject. Alternatively, stage 74 may include a transparent plastic material. Other transparent stages are suitable for use.

If a photographic image is desired from this position (505), then the imaging box and associated imaging components are then prepared for photographic image capture of the object.

Imaging preparation may initially include launching imaging and acquisition software (such as "LivingImage" software as provided by Xenogen Corporation of Alameda, Calif.) on a computer. Further preparations will depend on the imaging system and may include: initializing a camera, closing a door to the imaging chamber, activating the photographic capture option in the software, focusing the camera to a specific depth of the objector animal, and turning on lights in the imaging box. Hardware preparations may also include focusing a lens, selectively positioning an appropriate lens filter, setting the f-stop, etc. The imaging system then captures a photographic image from this view (508). Upon completion of photographic capture, the photographic image data is stored in memory or transferred to an image processing unit and/or a processor in an associated computer system.

If a structured light image is desired from this position (509), then the imaging components are then prepared for structured light image capture. This may include activating a structured light source, specifying structured light image capture parameters such as grid line density, etc. The imaging system then captures a structured light image (510). Upon completion of structured light capture, the structured light image data is stored or transferred for processing.

If desired (511), at the current viewing angle, process flow 500 then captures one or more low-intensity light images (512). A low-intensity light image typically includes one or more distinct low-intensity light portions of interest, such as where cancerous activity is a mouse is being monitored. The low-intensity light may include fluorescent and/or luminescent light, based on how light is produced in the object. Light from the light source refers to photons and electromagnetic energy anywhere in the visible to near-infrared (NIR) part of the spectrum in the wavelength range of 400-950 nm. It is understood that most internal light intensities are not readily detectable by human vision. For example, low intensity light emitted from a sample may have a surface radiance between about $10^3$ to about $10^{10}$ photons/second/centimeter squared/steradian or between about $10^3$ to about $10^8$ photons/second/centimeter squared/steradian, where the upper end of this latter range is below human detection levels.

Low-intensity light image capture and preparation may include selecting an exposure time and binning level using the computer, and turning off the lights in an interior cavity of the imaging chamber. When ready, the CCD camera captures the low-intensity light image over a set period of time (up to several minutes). The low-intensity light image data is transferred to memory, the image processing unit 26 and/or a processor in computer. Multiple low-intensity light images may be captured. For example, luminescent image capture at different wavelengths provides numerous data points for propagation of light from an internal source and through turbid flesh.

When luminescent imaging finishes at the current position, images may be captured from another view (520). While the object is at a next view relative to the camera, one or more photographic, structured light and/or luminescence images of the object are again captured (504-518).

The number of views captured for each modality may vary. In one embodiment, the present invention at least 6 photos around an object. In a specific embodiment, the present invention uses 12 photos spaced about every 30 degrees about a nose-to-tail axis of a mouse. Other numbers of photos may be taken and processed. As the number of images taken about the object increases, so does accuracy of the 3D topography. FIG. 5C illustrates the effect of increasing the number of views for 3D photographic topography. As shown, a 3D photographic topography 492 made from 6 photos (taken at angles equally about the circle) deviates noticeably from a perfect circle, while a 3D photographic topography 494 constructed from 12 photos deviates less. 3D photographic topographies made from 15 or 24 or more views will produce even more accurate representations. In one embodiment, the number of multiple views includes between about 4 and about 30 views of the object relative to at least one camera. The angles between photos may be equally spaced, or may include different angles, e.g., more images that show features with higher curvature or more images near important surface information.

Less structured light images may be used. Typically, structured light imaging captures a hemisphere of height data (or close to a hemisphere) that faces a camera. In many instances, one or two structured light images are enough (e.g., a dorsal and ventral view). More accurate embodiments may include from 3 to 8 structured light images, or more, depending on a desired level of accuracy. Multiple structured light images from different angles can be 'stitched together' to provide a full 3D representation, as will be described in further detail below.

The photographic images are then processed—for each angle and view—to generate a photographic mask in each image. The photographic mask refers to a 2D perimeter or shape of the object in an image, and may be represented and stored as a data structure or string of values for each image. The mask, or back-projection, resembles a 2D outline of the object that shows the object's outer shape in an image. Changing angles of the object relative to the camera gives different shapes of the object from different angles. Assembling the back-projections from photos of different angles provides a 3D topography. As described above, increasing the number of angles increases accuracy of a 3D back-projection photographic topography. FIG. 4 describes how a mask is obtained from a single image; FIGS. 5A-5C describe the assembly of multiple masks from different views to build a 3D topography.

The present invention uses a back-projection algorithm to determine a 2D outline or mask of an object in an image. FIG. 4 shows one exemplary back-projection algorithm 400 for obtaining a photographic mask from a photographic image in accordance with a specific embodiment of the present invention. Other back-projection algorithms and image processing techniques are suitable for use herein to build a 2D object mask from a photographic image. Several images 420 are shown adjacent to select steps 402-412 to help illustrate several image-processing steps of this specific back-projection algorithm.

Process flow 400 begins by receiving a photographic image of the object (402). In one embodiment, the image has already been cropped from a larger image to reduce the amount of information to be processed. If not, process flow 400 crops the image, if desirable, using any suitable cropping algorithm, many of which are know to those of skill in the art.

Various image-processing techniques are then used to identify the object relative to the background and to build a perimeter for the object. In one embodiment, image processing first cleans the histogram (color or black and white) for the image (404). Compressing the histogram or color bar often improves object detection within the histogram; log scale compression is suitable in this regard. Histogram shifts and other data manipulations may also be used.

Object information in the image is then differentiated from other information such as background information (406). Otsu's method is well suited to determine a threshold that separates the object from the other information, given only a histogram of pixel data in an image. The threshold is then applied to the image to eliminate the background information and generate an initial binary photographic mask. Other image processing techniques are known to those of skill in the art for finding an object in a photographic image and suitable for use in step 406.

Process flow 400 then cleans the initial photographic mask to improve quality (408). In one embodiment, this includes applying an open operation to remove spikes or noise along the edges of the object's photographic mask, and any other errant information in the image that passed the threshold such as the parallel lines as shown in FIG. 4 (produced by a transparent wire stage under the mouse). For example, an erosion and dilution will clean any spikes and noise in the image. Those of skill in the art are aware of erosion and dilution image processing algorithms, as well as other image-cleaning techniques that are suitable for use herein.

Regions in the image are then connected and labeled (410). Process flow 400 keeps the largest connected region in the image, and labels this largest connected region as the mouse. The connecting step further cleans the image by eliminating photographic information that was connected but disparate from the mouse.

Any holes in the connected mouse region are then filled (412) using a suitable filling algorithm. Output of this step is the object's photographic mask, which includes a 2-D perimeter of the object in the current image.

Process flow 400 is then repeated for each view (415).

Photographic 3D surface construction then takes the 2D masks from multiple views and builds a 3D surface for the object. FIGS. 5A-5C show topographic construction using photographic information in accordance with several embodiments of the present invention. In this case, the topographic construction uses back-projection reconstruction of multiple photographic images.

FIG. 5A shows the conversion of hardware parameters used in photographic image capture into a representative 3D space (in software) according to a 'pinhole' model. In hardware configuration 450, a camera 454 takes a picture of an object 456 that rests on stage 458. A mirror 462 and lens 464 facilitate image capture. The pinhole model knows the position of each of these image capture components and converts them into an equivalent 3D pinhole representation 451. The pinhole representation 451 maps the hardware coordinates of each image captured of object 456 on stage 458 into a 3D coordinate system used in software.

FIG. 5B shows the conversion of photographic information from different views to a common perspective. This adapts pinhole dimensions from different views into a common coordinate system so height information captured in each view can be assembled. In this case, image coordinates from the current view (x', z') are rotated to the common coordinates (x, z) to compensate for different angles of the camera relative to the object during imaging. Height information from the object in the current view is also rotated to give height information from multiple views in a single coordinate system. This permits all images taken in the imaging system, from any view of camera relative to the object, to be mapped into a common coordinate system, and allows object dimensions from multiple photographs, views and angles to be converted into a common 3D coordinate system in software. Conversion of photographic information from different views may include any combination of rotations and translations, depending on the known geometry of image capture equipment between views.

FIG. 6 illustrates a method 460 for photographic 3D surface construction in accordance with a specific embodiment of the present invention.

Topographic construction 460 first receives binary masks from multiple views of the object (462). Photos 480 are shown for 24 views of a mouse, taken about a nose-tail axis of the mouse. FIG. 4 shows one suitable method for producing a mask from each image. A 3D space is then set up to coordinate information from each view (464).

Each mask and image is processed in turn (468 and 473). For each mask, the topographic construction 460 converts mask coordinates (the shape of the object in a back-projected image) into a common coordinate system (470). The conversion includes at least one rotation and/or translation, based on the geometry of image capture equipment for this particular image (FIG. 5B).

Conversion includes altering each point in a mask to the common coordinate system (472). Points in the mask that were labeled as inside, or part of, the object are then used to assemble the object in the 3D space.

This process repeats for each point in the mask, and each view. Logic may be used to assemble the 3D object and photographic topography. In a specific embodiment, if a point is seen in all masks and views, it is labeled as part of the object in 3D; otherwise, if the point is not seen in any view, it is labeled as background or void.

After all views and points have been assessed, topographic construction 460 has an iso-surface, or a 3D structure that includes data at vertices that resemble spokes of a wheel normal to each viewing angle used. Topographic construction 460 then builds a surface for the object from the iso-surface (474) by connecting the vertices. This is shown by photographic surface topography 482.

Various topographic manipulations may then be used to improve the representation. A smoothing operation reduces stepwise appearance of the photographic topography. Corners may also be rounded to better approximate a real mouse. Output of topographic construction 460 includes surface vertices for the object in a 3D space, their connections, and a photographic topography of the object.

Structured light topographic construction will now be expanded upon.

Figure 7:
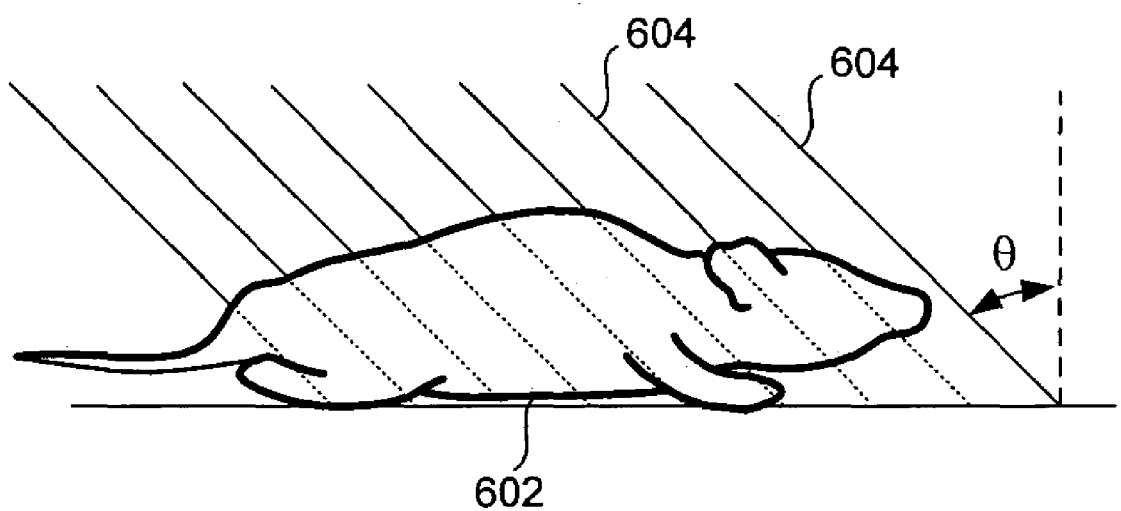
FIG. 7 illustrates the projection of structured light onto an object and the generation of structured light surface information.
Figure 8C:
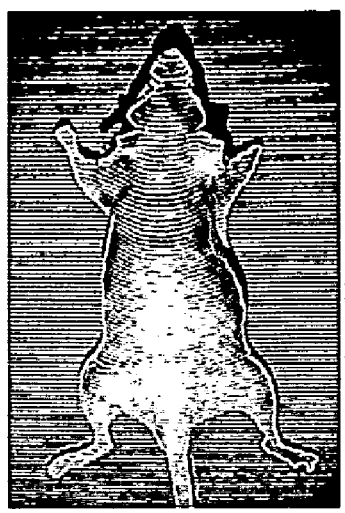

FIG. 7 illustrates the projection of structured light onto an object and the generation of structured light surface information. A structured light source transmits light onto an object 602 via multiple lines 404 at an angle, θ. Since the projection angle is known, horizontal displacement for each line 604 relates to the height of object 602. More specifically, the height of object 602 intercepts each line 604 and generates structured light information for each line 604 according to the horizontal displacement caused on the incoming light. By transmitting a grid of lines 604 of known dimensions onto the facing surface of object 602, quantitatively assessing horizontal deviations and bends in the captured light produces a map of the facing surface topography. FIG. 8C illustrates bends in a grid of lines cast onto a mouse. The structured light surface information then includes differences between a) the expected and known spacing for the transmitted array of lines without any interference and b) the observed pattern captured by a camera. Although the present invention will be described with respect to horizontal differences in the structured light for a horizontal surface normal, it is understood that other systems may transmit structured light from other angles to produce structured light information in another direction.

A structured light source produces the structured light 604 and includes a mechanism for transmitting a set of lines onto the object from an angle. Several suitable structured light sources are described in further detail below.

The angle of incidence relative to the surface normal may vary. In one embodiment, an angle, θ, from about 15° to about 30° is suitable. Angles greater or less than this range may also be used. Preferably, the projection angle is large enough to get sufficient "bend" in the lines to achieve spatial resolution, but small enough that large shadows are not present.

FIG. 8A illustrates a process flow 630 for structured light topographic reconstruction in accordance with a specific embodiment of the present invention. FIGS. 8B-8H illustrate pictorial representations of structured light imaging corresponding to process flow 630.

Structured light topographic reconstruction 630 begins by imaging a structured light reference (631 and FIG. 8B), which produces a structured light pattern without the sample. Applying structured light to a stage or surface that the object rests upon—before the object is imaged—accomplishes this. During structured light image capture, the stage then moves to the same locations as those used during reference data capture.

Subsequently, the object is imaged with structured light (632 and FIG. 8C). Structured light imaging casts a set of lines of light onto the object at an angle to a surface normal. The lines bend as they pass over the object; the bend in the lines quantifies height of the object and permits determination of surface height at all illuminated locations. In one embodiment, the casting angle is large enough to get sufficient "bend" in the lines to achieve spatial resolution, but small enough that large shadows are not present. Angles between 10 degrees and 50 degrees are suitable for use in this regard. Other casting angles may be used.

Figure 8D:
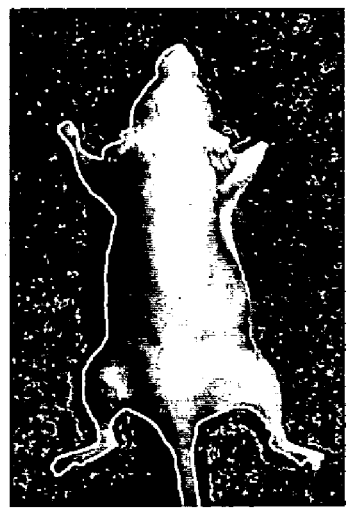
Figure 8E:
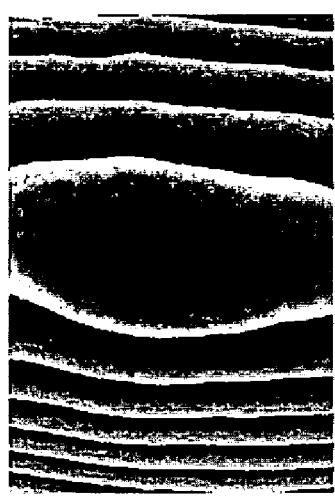

Process flow 630 then proceeds by imaging the sample without structured light (633 and FIG. 8D).

The structured light processing then determines a phase shift and then unwrap the phase to get a surface mesh, or height map. A reference, or background, surface is subtracted from the object surface, to yield the final surface. In one embodiment, the phase shift of each line at all points on the background and object may be determined from a 2D Fourier transform. To obtain a reference, the background data is then converted to a wrapped phase (634 and FIG. 8E). Here, the background data is Fourier transformed and filtered before calculating a wrapped phase. Similarly, the object structured light data is converted to a wrapped phase (635 and FIG. 8F) by Fourier transforming and filtering the object structured light data, and the calculating a wrapped phase for the object structured light data.

Figure 8F:
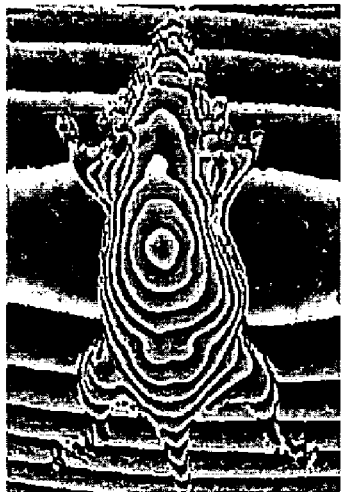
Figure 8G:
Figure 8H:
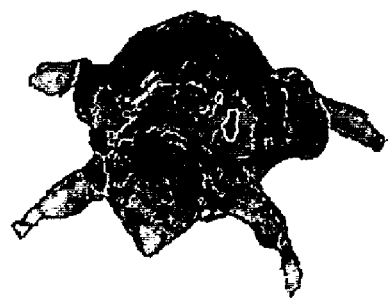

Process flow 630 then calculates structured light surface topography for the object (636 and FIG. 8G). In this case, "unwrapping" the phase map performs this. Several unwrapping algorithms are available to those of skill in the art for this task. For example, the phase shift of each line at all points on the image can be determined from using Fourier profilometry techniques. With these methods, a 2D Fast-Fourier transform (FFT) of the fringe data (FIG. 8D) is taken to determine the phase shift of the lines everywhere in the image (FIG. 8F). Since the phase will shift by many multiples of $2\pi$ for a typical object, the phase exhibits $2\pi$ jumps as seen in FIG. 8F. These phase jumps are "unwrapped" in order to determine the structured light surface topography.

In one embodiment, the present invention also produces quality characterizations of the structured light data. For example, clear and sharp structured light lines may be labeled as 'high quality', while unclear or disturbed structured light lines marked with 'low quality' (e.g., unclear structured light data impeded by mouse hair). Low quality structured light often appears in regions of high curvature, such as the arms and legs of the mouse or in regions with rough fur.

The quality may be quantified (e.g. a numerical value). For example, high quality may be designated as a '1', while low quality earns a '−1'; other numerical representations may be used. A quality map refers to an assignment of quality for the structured light lines in a structured light image, and may be represented with a pixel-based array of quality for the image.

FIG. 9 illustrates a method 700 for modifying a structured light image using quality in accordance with a specific embodiment of the present invention. Input for method 700 includes a structured light image and a quality map for the structured light image.

Method 700 begins by thresholding the quality map to create a quality mask (702). The quality mask is later applied to keep quality structured light data in an image—and discard the poor structured light data. For example, thresholding may keep the top 90% of structured light quality numbers in a quality map. When the quality mask is applied to its corresponding structured light image, this discards the bottom 10% of structured light data in the image. As will be described below, this discarded height information may be recaptured from the photographic height data when the structured light data and photographic topography are combined. Other percentage cutoffs, thresholding techniques and quality measures may be used on the quality map, as one of skill in the art will appreciate. The output of this step is a quality mask that is used to selectively discard structured light data based on structured light data quality.

The quality mask is then applied to structured light data in the structured light image (704). This eliminates regions of the structured light image with poor quality and maintains quality height information.

Method 700 then applies one or more image processing procedures to clean the image (706). For example, an open operation (e.g. an erosion then a dilution) may be applied to edges in the structured light data to remove discrepancies along the edges of the object in the structured light image.

Regions in the structured light image are then connected and labeled (708). Method 700 keeps the largest connected region in the structured light image, and labels this region as the mouse. This step also cleans the structured light image by eliminating structured light data that was connected and disparate from the mouse. Any holes in the connected mouse region are then filled (710) using a suitable filling algorithm.

Method 700 then finds a perimeter of the mouse in the image (712). In one embodiment, perimeter detection subtracts the mouse data in the image from a dilation of the mouse (the dilation makes the mouse slightly bigger in 2D) to produce an outline of the mouse. Other edge detection techniques are known to one of skill in the art and may be employed to find a mouse perimeter in a 2D image, such as a Sobel mask for example. The object perimeter is then marked and stored. Output for method 700 includes a qualified structured light topography and a border for the object.

The dual modality topographic construction now compares and combines the structured light topography and photographic topography.

Synchronizing the structured light information and the photographic information (214 from FIG. 2) first overcomes any offset in the dual modality information between shape or position of the object as determined in structured light imaging relative to the shape or position of the object as determined in photographic imaging. This co-registration accounts for any difference in size and/or location between topographies produced in the structured light and photographic modalities. In one embodiment, the vertices found in each modality provide a start for the relative position and shape of the mouse from each modality. Comparing slopes in the height information between the two modalities, and altering the position of the mouse in one of the modalities to match the slopes, improves the relative positioning between the modalities. Minimizing a least squares error for the slopes provides one technique for automated comparison of the locations. Mouse location in one of the modalities is then altered (rotated, translated, etc.) to match location between the two. Output of this step includes labels for all surface vertices under a common 3D coordinate system and co-registered planar coordinates normal to the height information. For example, each modality may be labeled with x,y,z coordinates where the x and y coordinates refer to planar coordinates of an image while the z coordinate refers to height of the object. The x,y coordinates are co-registered for the structured light information and the photographic information, which permits comparison of the z-height information.

The height information from both modalities is then compared and merged to provide a dual modality topographic representation (216 from FIG. 2). This includes one or more comparisons. In one embodiment, the merge includes replacing the height of labeled surface vertices in the photographic topography with the height given by structured light height maps, which are generally more accurate. In another embodiment, the photographic topography height information is used in locations where the structured light height maps lacked quality. For a mouse, one or more smoothing operations may also be applied to create a less stepwise and softer representation that includes no spikes or overly sharp features.

Images from multiple views, or the partial surfaces obtained from each view, may also be combined to form a more complete 3D surface. For example, non-linear least squares fitting techniques minimize the distance between mesh elements on two surfaces being connected and permit registration of multiple views. Another registration technique uses an absolute reference line or fiducial of some kind from all images, which gives an absolute position of any partial surface. If the absolute positioning of each surface is accurate enough, then the non-linear fitting method described above can be skipped.

A surface topography provided herein has many uses. Some users may employ the surface topography to provide a pictorial view of the object surface. This larger 3D topography permits use by software programs that allow the object to be rotated and viewed from multiple sides and angles.

The surface topography may also be used in tomographic reconstruction of an internal light source. One suitable reconstruction algorithm (or inversion algorithm) is diffuse optical tomography. Diffuse optical tomography uses a 3D surface topography of the object to map a bioluminescent emission onto this 3D surface. The tomography determines photon density just below the surface using: a) one or more luminescent images that include luminescent data relating to light that escapes from a surface of the object and emitted from a light source internal to the object, and b) the surface topography or a surface mesh. The photon density just below the surface relates to light intensity emitted from the surface and captured in the luminescent images. A set of volume elements represents the volume interior to the surface. The source strength in each volume element then determines photon density just below the surface, and the internal light source of interest. The tomographic reconstruction outputs a 3D representation of the internal light source.

Together, the topographic reconstruction and luminescent tomographic representation may be combined to form a superposition or 3D overlay image, with the luminescent data typically shown in pseudocolor to visually characterize intensity. This 3D overlay image permits user analysis, such as an analysis that sums illumination magnitudes over pixels within a portion of the overlay image.

The present invention may be employed in a wide variety of imaging applications. In one embodiment, the topographic reconstruction is applied in a non-invasive method for detecting, localizing and tracking light-emitting entities and biological events in a mammalian subject.

Low light level imaging, such as bioluminescent or fluorescent imaging, is a non-invasive technique for performing in vivo diagnostic studies on animal subjects in the areas of medical research, pathology and drug discovery and development. Bioluminescence is typically produced by cells that have been transfected with a luminescent reporter such as luciferase and can be used as a marker to differentiate a specific tissue type (e.g. a tumor), monitor physiological function, track the distribution of a therapeutic compound administered to the subject, or the progression of a disease. A wide range of applications has been demonstrated including areas of oncology, infectious disease, and transgenic animals. Labeling cells with fluorescence can also be achieved using green fluorescent proteins (GFP) or dyes such as Cy5.5.

Figure 10A:
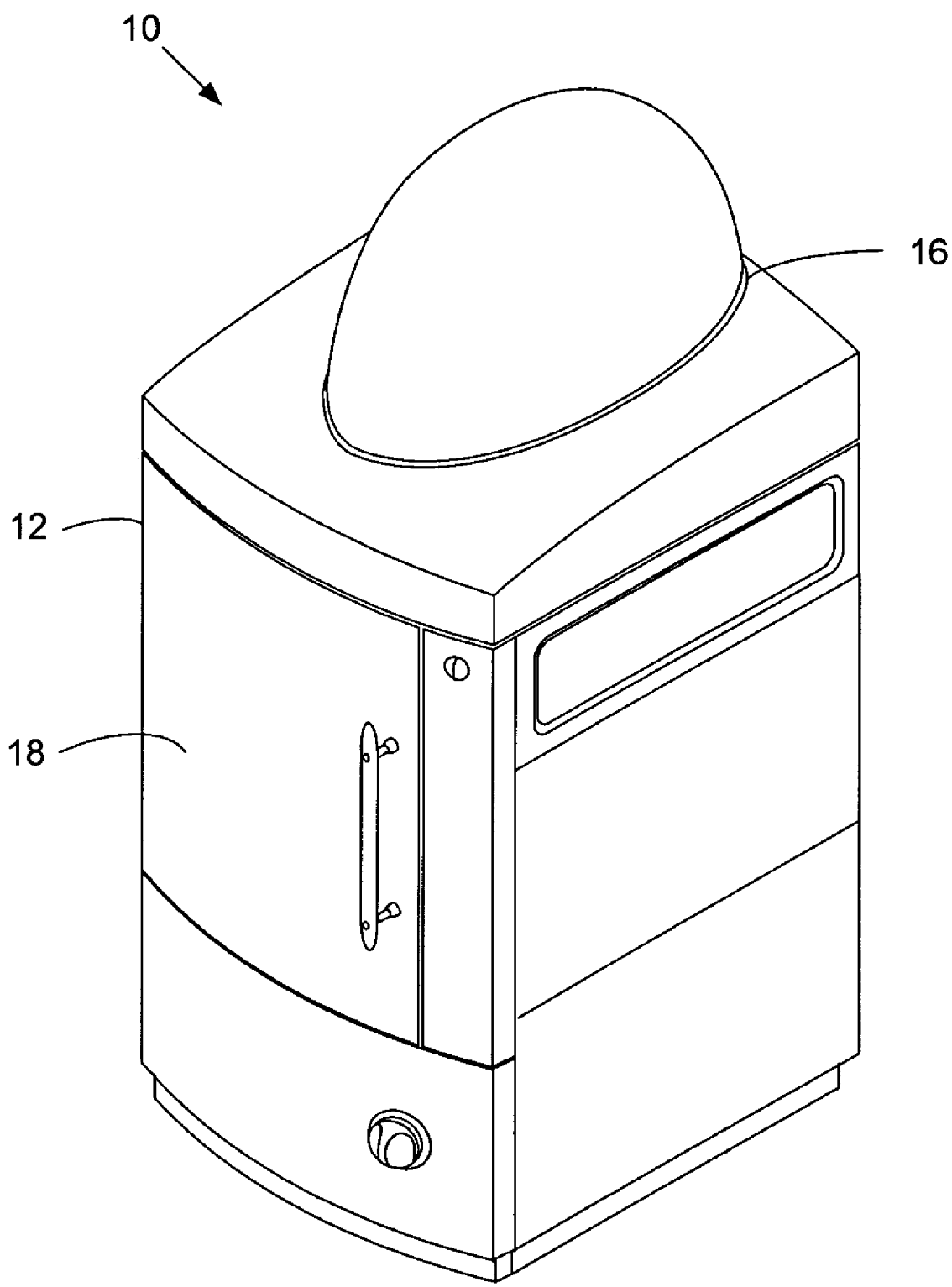
FIG. 10A is a perspective view of an imaging system including an imaging box adapted to capture images in accordance with one embodiment of the invention.
Figure 10B:
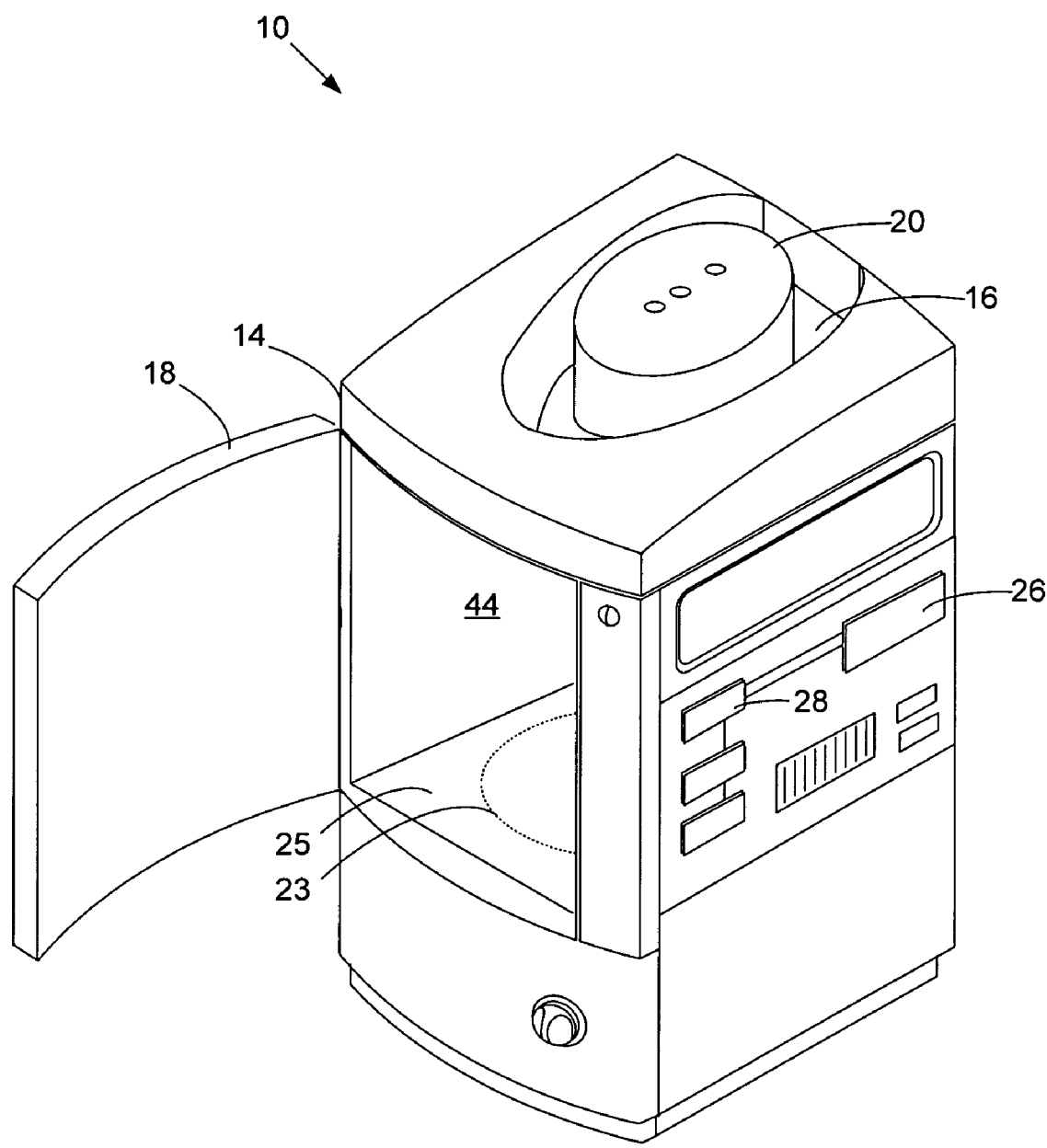
FIG. 10B illustrates internal components for the imaging box of FIG. 10A.

The present invention also relates to dual modality imaging systems that generate a topographic representation of an object. FIGS. 10A and 10B illustrate an imaging system 10 adapted to capture photographic, structured and/or luminescence images in accordance with one embodiment of the present invention.

Imaging system 10 captures photographic and structured light images, and includes processing capabilities to build dual modality topographic representations. System 10 also permits user-automated control of image capture in an imaging box 12. Imaging system 10 comprises an imaging box 12 adapted to receive a light-emitting object in which low intensity light, e.g., luciferase-based luminescence, is to be detected. Imaging box 12 includes a housing 16 on a top wall of the box having a camera mount 16 adapted to receive a camera. Imaging box 12 is configured to be "light-tight", i.e., essentially all external light is prevented from entering the box 12 from the ambient room.

A high sensitivity camera, e.g., an intensified or a charge-coupled device (CCD) camera 20, attaches to imaging box 12 preferably through a camera mount affixed to housing 16. CCD camera 20 captures photographic, structured light and luminescent images of the object within the imaging box 12. CCD camera 20 may optionally be cooled by a suitable source such as a refrigeration device 22 that cycles a cryogenic fluid through the CCD camera via conduits 24. A suitable refrigeration device is the "CRYOTIGER" compressor, which can be obtained from IGC-APD Cryogenics Inc., Allentown, Pa. Other refrigerants, such as liquid nitrogen or solid state devices, may be used to cool the CCD camera 20.

Processing system 28 is configured to produce a three-dimensional surface representation of an object using photographic and structured light surface information obtained by camera 20. Processing system 28, which may be of any suitable type, is included in the stand-alone box of system 10 and typically includes a processor, memory components such as random-access memory (RAM) and read-only memory (ROM), and disk drive components (e.g., hard drive, CD, floppy drive, etc.). In another embodiment, processing system 28 is included in a separate and commercially available computer that also includes a display and input devices such as a keyboard and mouse. Processing system 28 may also include additional imaging hardware and software, structured light software, and image processing logic and instructions for processing information obtained by camera 20.

Typically, a processor produces the 3D surface representation using instructions stored in memory that determine how to produce the 3D surface representation from one or more images. For example, stored instructions run by processing system 28 may include instructions for i) receiving photographic and structured light information, and ii) building a 3D topographic representation of the object in box 12 using photographic and structured light information obtained by camera 20 while the animal rests on a stage, etc. Processing system 28 also includes suitable processing hardware and software for camera 20 such as additional imaging hardware, software, and image processing logic for processing information obtained by camera 20. An optional image processing unit 26 interfaces between camera 20 and processing system 28.

The logic in processing system 28 may take the form of software, hardware or a combination thereof. System 28 may also communicate with a display device for presenting imaging information to a user. By way of example, the display may be a monitor, which presents a measurement graphical user interface (GUI). The graphical user interface allows a user to view imaging results and also acts an interface to control the imaging system 10. One suitable imaging software includes "LivingImage" as provided by Xenogen Corporation of Alameda, Calif.

To provide control of various components, processing system 28 also includes processing hardware and software configured to provide output for controlling any of the devices in the imaging box 12. The processing hardware and software may include an I/O card, control logic for controlling any of the components of the imaging system 10, and a suitable graphical user interface for the imaging system 10. Components controlled by processing system 28 may include camera 20, the motors responsible for camera 20 focus, one or more motors responsible for position control of a stage 23 supporting the object, a camera lens, f-stop, etc.

Imaging system 10 is suitable for capturing images from a variety of positions of the object relative to camera 20. These images may be used in in-vivo imaging applications that include analysis of one or more representations of emissions from internal portions of a specimen superimposed on a photographic representation of the specimen. In one embodiment, imaging system 10 is used for 2-D, 3D and structured light imaging of a low intensity light source, such as luminescence from luciferase-expressing cells, fluorescence from fluorescing molecules, and the like. The low intensity light source may be emitted from any of a variety of light-emitting objects which may include, for example, tissue culture plates, multi-well plates (including 96, 384 and 864 well plates), and animals containing light-emitting molecules. Animals may include any mammal, such as a mouse, cat or rat for example.

In one embodiment, the object is a mouse containing light producing cells. A luminescence image may be captured without using any light sources other than the object itself. Luminescence from the object is recorded as a function of position to produce the luminescence image. One approach to generating such composite photographic/luminescence images is described in U.S. Pat. No. 5,650,135 issued to Contag et al. on Jul. 22, 1997. The entire disclosure of that patent is incorporated herein by reference for all purposes.

In one particular embodiment, a 2-D or 3D luminescence image represents a collection of emitted photons received by each detector pixel of the CCD camera 20 over a defined length of time. Regions of the object emitting radiation (e.g., photons) will appear in the luminescence image. The luminescence images may indicate the presence of a biocompatible entity, for example. The entity can be a molecule, macromolecule, cell, microorganism, a particle or the like. Thus, an in-vivo analysis may include detecting localization of a biocompatible entity in a mammalian subject.

System 10 may provide both topographic and tomographic imaging. Tomographic imaging refers to information inside the surface. This is useful for localizing internal objects in three dimensions inside an object, for example. An exemplary illustration of these two imaging forms uses a 2D planar slice through an object: topography gives the surface (the outer bounding line), while tomography gives everything inside the bounding surface.

As shown in FIG. 10B, imaging box 12 is illustrated with a door 18 in an open position, showing an imaging chamber 44 for receiving the object. Imaging chamber 44 is defined by opposing side enclosure panels, a light-tight partition on the bottom, a top panel and a back enclosure panel (not shown), and a front wall on door 18 that defines a cavity opening into the imaging chamber 44.

Below chamber 44 is a smaller compartment separated therefrom by the light-tight partition 23, the upper surface of which serves as a floor for imaging chamber 44. In one embodiment, the smaller compartment provides a housing space that is adapted to slideably receive a drawer though a front opening. The drawer houses electronic components which are in electrical communication with processing system 28 and control various components and functions of the box 12. In a specific embodiment, the imaging box 12 has a body made of a suitable metal such as steel.

A latchable door 18 pivotally attaches to box body 14 by way of hinges which permit the door 18 to be moved from the closed position as shown in FIG. 10A to the open position as shown in FIG. 10B. In the open position, door 18 enables user access to the cavity 44 through the opening so the user can place an object on stage 23. In the closed position, door 18 prevents access to the cavity 44 and provides a light-tight seal for cavity 44.

Xenogen Corporation of Alameda, Calif., provides several imaging systems suitable for use with the present invention; these include the IVIS-200 and IVIS 3D series of imaging systems. Other imaging systems are also suitable for use herein.

In one embodiment, the object is placed on a moveable stage. The moveable stage allows an image of the sample, or portions thereof, to be captured by a camera from different views, angles, and positions within the imaging box 12 without repositioning the object. In one embodiment, the moveable stage permits 1 degree of freedom motion relative to the camera (e.g., FIG. 11), which is suitable for structured light imaging. In another embodiment, the moveable stage permits 2 degree of freedom motion relative to the camera (e.g., FIG. 12A-12C), which is suitable for structured light and/or multiview photographic imaging.

Figure 11:
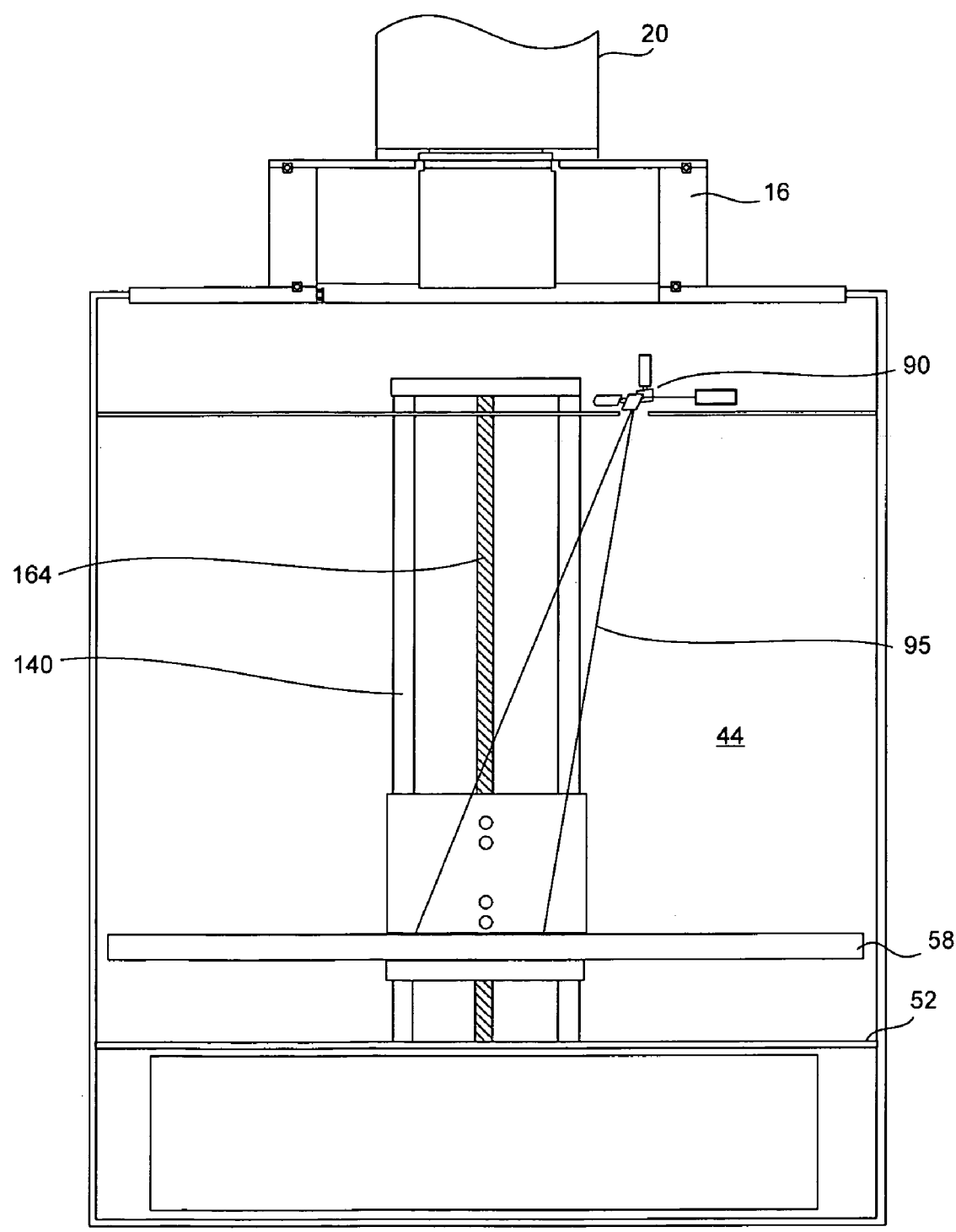
FIG. 11 illustrates a stage internal to an imaging box that includes a scanning laser galvanometer in accordance with a specific embodiment of the present invention.

FIG. 11 illustrates a simplified cross section of a moveable stage 58 internal to an imaging box that includes a scanning laser galvanometer 90 in accordance with one embodiment of the present invention.

Movable stage 58 supports the object to be imaged. As the term is used herein, a stage refers to a structure used to support an object during image capture. Flat surfaces are well suited for use, such as a fixed flat bottom panel in the imaging box (a stationary stage). Some stages may include transparent portions to permit image capture through the stage.

Movable stage 58 is capable of linear, reciprocal movement between a bottom partition 52 and a top enclosure panel, and may be retained at any position therebetween for image capture. Thus, moveable stage 58 has a multiple vertical positions in imaging chamber 44 having the substantially same horizontal position. In a specific embodiment, movable stage 58 has a threaded bore that is operably engaged with a worm gear 164 that provides vertical translation of the moveable stage 58. A motor drives the worm gear to move the stage 58 up and down along a pair of guides 140.

In one embodiment, the present invention builds a surface topography of the animal for a large surface of the animal that is greater than just the surface facing the camera. In this case, imaging system 10 captures a sequence of images from multiple positions and different viewing angles. FIGS. 12A-12C illustrate one system suitable for obtaining images from multiple viewing angles.

A moveable stage apparatus 75 is disposed in interior cavity 44, and includes a transport mechanism 72 and a stage 74 to support a light-emitting object 76. Moveable stage apparatus 75 is capable of two degrees of freedom movement to reposition the stage 74 (and object 76) to a plurality of positions within interior cavity 44. Two linear actuators 72, oriented substantially perpendicular to one another, move stage 74 according to control signals provided by a processor.

Light transmission device 71 directs light reflected or emitted from object 76 along the direction of a fixed datum for image capture by camera 20. Light transmission device 70 assists image capture for a fixed camera 20 by transmitting light emitted or reflected from the variably located object 76 to a common datum associated with a fixed camera 20 (on a sidewall of imaging box 12). Light transmission device 71 is mounted to housing 16 using stationary bracket 81 (FIG. 12B), which includes circumferentially disposed bearings between stationary bracket 81 and a moving bracket 83 that allow turning mirror assembly 70 to rotate freely relative to stationary bracket 81.

Figure 12A:
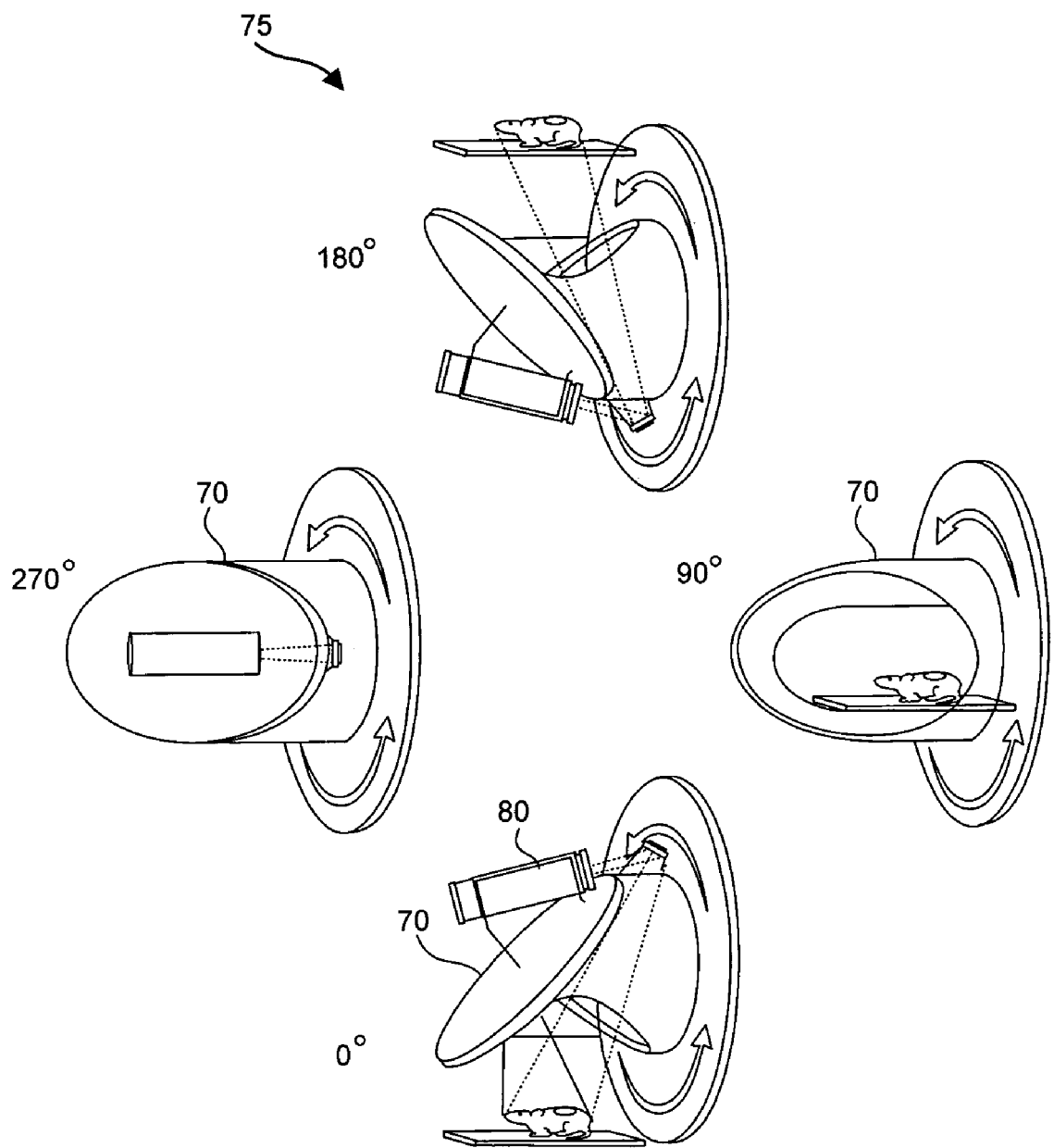
FIG. 12A shows four different positions of a stage relative to a light transport device for the imaging system of FIG. 12B.
Figure 12B:
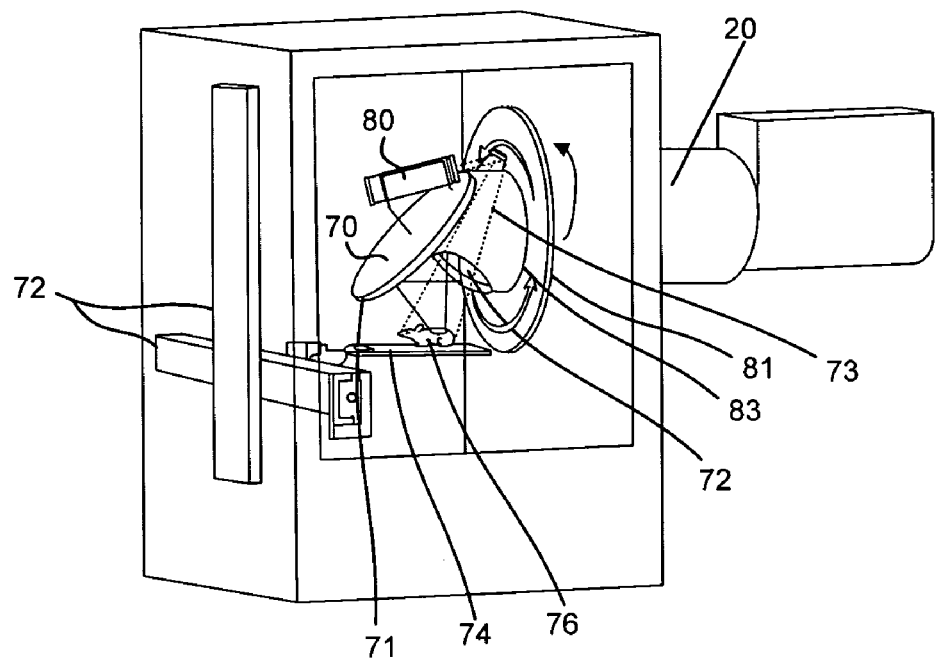
FIG. 12B is a cut away perspective view of an imaging system having internal components for facilitating multiple views of the sample in accordance with one embodiment of the present invention.
Figure 12C:
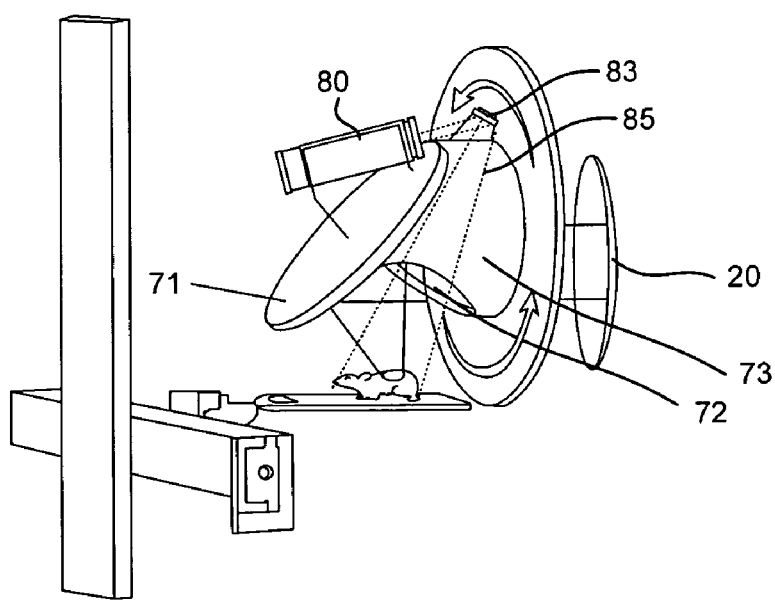
FIG. 12C is a perspective view of the internal components of the imaging system of FIG. 12B for facilitating multiple views of the sample in accordance with one embodiment of the present invention.

Referring to FIG. 12C, mirror assembly 70 comprises an angled mirror 71 that reflects light from object 76 on stage 74 in a direction along fixed datum (perpendicular to the wall that supports camera 20) and into camera 20. Outer wall 73 is substantially cylindrical and includes aperture 72 that enables light to pass between stage 74 and turning mirror 71. As stage 74 is positioned along the circular path about the stationary axis by actuators 72, outer wall 73 and turning mirror 71 cooperate to collect light primarily from the angular direction of stage 74 which is then reflected along the fixed datum for reception by camera 20.

The two-degree of freedom movement provided by transport mechanism 72 allows stage 74 and object 76 to be positioned at multiple angles relative to the fixed datum that passes light to camera 20. Thus, based on user input, transport mechanism 72 and light transmission device 71 cooperate to direct light from object 76 on stage 74 to camera 20. In addition to providing fill 360 degree angular viewing of object 76 about the circular path (see FIG. 12A), transport mechanism 72 is capable of varying the image depth for a given angle of stage 74. Similar to the user initiated angular position control described above, a user may input a desired focal depth and viewing angle for stage 74. Software included in computer 28 and linear actuators 72 would then combine to position stage 74 and turning mechanism 70 at the desired angle and depth relative to the fixed datum and camera 20.

Figure 13:
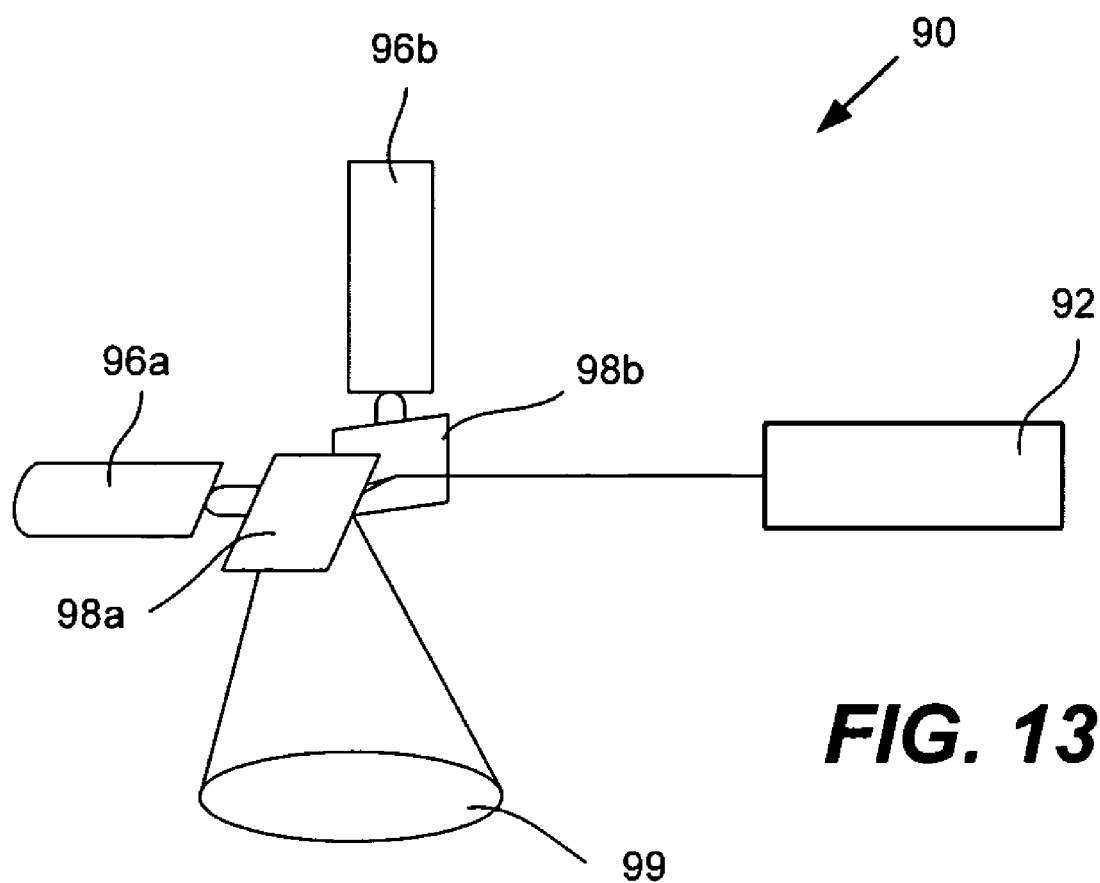
FIG. 13 illustrates a structured light source comprising a scanning laser galvanometer in accordance with one embodiment of the present invention.

Imaging systems of the present invention also include a structured light source. In one embodiment, the structured light source includes a projector that projects a grid of lines onto the object (FIGS. 12A-12C). In another embodiment, a structured light source includes a laser whose output is steered by a pair of actuated mirrors, which rapidly move the laser beam to form a set or grid of lines across the object (FIGS. 11 and 13). Another suitable structured light projector comprises a laser device that employs diffraction patterns to achieve a desired structured light pattern. Other structured light sources may be used with the present invention.

FIGS. 11 and 13 illustrate a scanning laser galvanometer 90 in accordance with a specific embodiment of the present invention. Referring to FIG. 11, scanning laser galvanometer 90 is disposed at the top of imaging chamber 44 and reflects structured light 95 down onto a top surface of the animal. Referring to FIG. 13, scanning laser galvanometer 90 comprises a laser 92 and a pair of mirrors 98a and 98b, and projects structured light onto the top surface of stage 58. The grid size produced on stage 58 (or an animal resting thereon) will depend on position of stage 58 and control of each mirror 98 according to a desired grid size.

Laser 92 generates light. Mirrors 98 each direct light provided by laser 92. The two mirrors 98 cooperate to provide two degree of freedom control for positioning a light beam provided by laser 92. A maximum transmission field 99 defines the spatial range for direction of light by scanning laser galvanometer 90. Actuators 96a and 96b position mirrors 98a and 98 respectively, and may create any line, shape, grid or pattern of light within field 99. For example, actuators 96 and mirrors 98 may form a set of parallel lines normal to the head to toe facing of a mouse (for any position of the mouse).

In another embodiment, the structured light source includes a light projector. FIGS. 12A-12C illustrate a structured light projector 80 in accordance with a specific embodiment of the present invention. Structured light projector 80 comprises a light source and a filter or mask that creates a structured light pattern. In this case, structured light projector 80 includes a Kohler illumination system where a slide is illuminated by a light source and then an image of the slide is projected onto the sample or background. As shown in FIG. 12C, structured light 85, emitted from structured light projector 80, reflects off a mirror 83, and passes onto the object 76. The structured light 85 may then be captured by camera 20.

FIG. 12A shows structured light projector 80 attached to and rotating with light transport device 70. The projector module 80 rides on the back of the rotating light transport device 70 so that lines are always projected on the object 76 at all viewing angles. The illumination pattern is projected horizontally and reflects off of a projector mirror 83 (FIG. 12C) at the base of the larger turning mirror to illuminate object 76.

In general, the light output by a structured light source may include any lines or shapes suitable for generating structured light surface information that is useful in building a surface topography. In one embodiment, a structured light source transmits a grid of lines onto the animal. Spacing between lines in a parallel grid may be adapted to a specific object or image. A parallel grid of lines having line spacing in the range of about 0.2 to about 2 lines per mm is suitable for a mouse. Other line spacings are suitable for use with the present invention. The line spacing may vary based on the object surface texture and object size. Closer line spacing provides higher resolution. As mentioned above photographic information may be used offset limitations of structured light at high resolutions, thus enabling even closer spaced structured light lines and more accurate surface representations.

Although topographic reconstruction has been described so far with respect to methods and apparatus, the present invention also relates to machine-readable media that include program instructions, state information, etc. for performing topographic reconstruction such as those described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). A processor as described above may then be configured to run from the stored instructions and perform many of the methods described above. Examples of program instructions include both machine code, such as produced by a compiler, and files containing higher level code that may be executed by the computer using an interpreter.

While this invention has been described in terms of several preferred embodiments, there are alterations, permutations, and equivalents that fall within the scope of this invention which have been omitted for brevity's sake. It is therefore intended that the scope of the invention should be determined with reference to the appended claims.

What is claimed is:

1. A method of constructing a topographic representation of at least a portion of an object; the method comprising:
   obtaining at least one photographic image of the object that includes photographic information wherein the object includes a flexible surface, a non-solid surface or combinations thereof;
   obtaining a structured light image of the object that includes structured light information;
   assessing quality in the structured light image to separate quality portions of the structured light image from other portions not suitable for further processing according to an image quality threshold;
   processing only the separated quality portions of the structured light image further to produce a quality thresholded structured light image; and
   constructing the topographic representation of at least the portion of the object using a combination of topographic information from the structured light image and topographic information from the photographic image, wherein said constructing includes replacing data from the photographic information with quality thresholded structured light information data.

2. The method of claim 1, further comprising:
   generating a quality mask that indicates portions of the structured light image that include low quality structured light information; and
   applying the quality mask to the structured light information to eliminate the low quality structured light information.

3. The method of claim 2 wherein creating the topographic representation includes replacing the low quality structured light information with the photographic topographic information.

4. The method of claim 1 wherein the photographic information is processed using back-projection to determine the surface topography.

5. The method of claim 1 wherein the structured light information includes topographic information in a concave feature of the object.

6. The method of claim 1 further comprising capturing low intensity light emitted from within the object due to presence of a bioluminescent or fluorescent marker.

7. The method of claim 6 wherein the object has a surface radiance between about $10^3$ to about $10^{10}$ photons/second/centimeter squared/steradian.

8. The method of claim 1 wherein the object is a living mammal.

9. The method of claim 8 wherein the mammal is a mouse.

10. The method of claim 1 wherein said constructing the topographic representation includes using the photographic information to construct a rough frame of the object, and then using more accurate height information from the structured light information in locations where the structured light quality is good to construct inner details of the object.

11. The method of claim 1 further including the step of:
    smoothing the topographic representation to account for slope omissions or discrepancies, to reduce a stepwise appearance, or both.

12. The method of claim 11 wherein said smoothing includes rounding corners on the topographic representation.

13. The method of claim 1 further including the step of:
    processing the photographic information to differentiate the object from one or more other items in the photographic image; and
    removing information on said one or more other items from the photographic information.

14. The method of claim 1 further including the step of:
    processing the photographic information to fill holes within the outer perimeter of said object.

15. The method of claim 1 further including the step of:
    converting photographic information from different camera angles to a common virtual three-dimensional coordinate system to compensate for different camera angles.

16. The method of claim 1 further comprising co-registering the structured light information and photographic information.

17. The method of claim 1, wherein the flexible surface includes skin of an animal.

18. The method of claim 1, wherein the non-solid surface includes fur of an animal.

19. A method of constructing a topographic representation of at least a portion of an object; the method comprising:
    obtaining multiple photographic images of the object that correspond to multiple views of the object relative to at least one camera wherein the object includes a flexible surface, a non-solid surface or combinations thereof;
    constructing a topographic representation of at least a portion of the object by processing the multiple photographic images using a back-projection algorithm;
    obtaining a structured light image that includes topographic information of the object;
    assessing quality in the structured light image to separate quality portions of the structured light image from other portions not suitable for further processing according to an image quality threshold;
    processing only the separated quality portions of the structured light image further to produce a quality thresholded structured light image; and
    constructing the topographic representation of at least the portion of the object using a combination of the structured light topographic information and topographic information from the photographic topographic representation, wherein said constructing includes replacing data from the photographic information with quality thresholded structured light information data.

20. The method of claim 19 wherein the multiple views include between about 4 and about 30 views of the object relative to at least one camera.

21. The method of claim 19 wherein the multiple views are obtained by moving a stage, that the object rests upon, relative to the at least one camera.

22. The method of claim 19 further comprising obtaining a second structured light image for a different view of the object.

23. The method of claim 22 further comprising stitching together topographic representations for the first structured light image and the second structured light image.

24. An imaging system for creating a topographic representation of at least a portion of an object; the system comprising:
- at least one camera configured to capture a photographic image of the object wherein the object includes a flexible surface, a non-solid surface or combinations thereof;
- a structured light source adapted to cast structured light onto the object and generate structured light information; and
- a processor that uses instructions stored in memory to construct the topographic representation of at least the portion of the object using a combination of topographic information from a structured light image captured by the at least one camera when structured light is cast onto the object and topographic information from a photographic image captured by the at least one camera, wherein said processor is adapted to assess quality in the structured light image to separate quality portions of the structured light image from other portions not suitable for further processing according to an image quality threshold, to process only the separated quality portions of the structured light image further to produce a quality thresholded structured light image, and to replace data from the photographic information with quality thresholded structured light information data.

25. The system of claim 24 further including an imaging chamber adapted to receive the object during photographic image capture with the at least one camera.

26. The system of claim 25 wherein the at least one camera includes a single camera that is attached to a wall of the imaging chamber.

27. The system of claim 24 wherein the structured light source includes a laser scanning galvanometer.

28. The system of claim 27 where the structured light source consists of an LED illuminated grating that is optically projected onto the subject.

29. A non-transitory computer readable medium including processor executable instructions for creating a topographic representation for at least a portion of an object, the instructions comprising:
- instructions for obtaining at least one photographic image of the object that includes photographic information wherein the object includes a flexible surface, a non-solid surface or combinations thereof;
- instructions for obtaining a structured light image of the object that includes structured light information;
- instructions for assessing quality in the structured light image to separate quality portions of the structured light image from other portions not suitable for further processing according to an image quality threshold;
- instructions for processing only the separated quality portions of the structured light image further to produce a quality thresholded structured light image; and
- instructions for constructing the topographic representation of at least the portion of the object using a combination of topographic information from the structured light image and topographic information from the photographic image, wherein said constructing includes replacing data from the photographic information with quality thresholded structured light information data.

* * * * *